(12) United States Patent
Watterson et al.

(10) Patent No.: US 8,278,305 B2
(45) Date of Patent: Oct. 2, 2012

(54) MYOSIN LIGHT CHAIN KINASE INHIBITOR COMPOUNDS, COMPOSITIONS AND RELATED METHODS OF USE

(75) Inventors: Daniel Martin Watterson, Douglas, MI (US); Linda J. Van Eldik, Lexington, KY (US); Heather Behanna, Chicago, IL (US); Hantamalala Ralay Ranaivo, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/786,676

(22) Filed: May 25, 2010

(65) Prior Publication Data

US 2010/0240668 A1 Sep. 23, 2010

Related U.S. Application Data

(62) Division of application No. 11/880,541, filed on Jul. 23, 2007, now Pat. No. 7,732,445.

(60) Provisional application No. 60/832,372, filed on Jul. 21, 2006.

(51) Int. Cl.
*A61K 31/525* (2006.01)
*C07D 237/00* (2006.01)
(52) U.S. Cl. .................. 514/252.05; 514/248; 544/224
(58) Field of Classification Search .................. 514/248, 514/252.05; 544/224
See application file for complete search history.

(56) References Cited

U.S. PATENT DOCUMENTS 7,312,246 B2 12/2007 Hamilton et al.

FOREIGN PATENT DOCUMENTS

WO 03018563 3/2003

OTHER PUBLICATIONS

Shin, et al., (2009), PLoS One 4(10): e7451. doi:10.1371/journal.pone.0007451.*
Barkan, et al., Academia, edu, 2008, downloaded Feb. 28, 2011, http://scripps.academia.edu/edcho/Papers/177139/Inhibition_of_Metastatic_Outgrowth_from_Single_Dormant_Tumor_Cells_by_Targeting_the_Cytoskeleton.*
Duxbury, et al., Biochem. & Biophys. Res. Commun., vol. 313, # 4, Jan. 23, 2004, pp. 992-997.*
Rossi, J; Bayram, M; Udelson, JE; Lloyd-Jones, D; Adams, KF; Oconnor, CM; Gattis Stough W; Ouywang, J; Shin, DD; Orlandi, C; Gheorghiade, M. Improvement in hyponatremia during hospitalization for worsening heart failure is associated with improved outcomes: insights from the Acute and Chronic Therapeutic Impact of a Vasopressin Antagonist in Chronic Heart Failure (ACTIV in CHF) trial. Acute Cardiac Care. 2007; 9: pp. 82-86.
Haorah, J; Heilman, D; Knipe, B; Chrastil, J; Leibhart, J; Ghorpade, A; Miller, DW; Persidsky, Y. Ethanol-Induced Activation of Myosin Light Chain Kinase Leads to Dysfunction of Tight Junctions and Blood-Brain Barrier Compromise. Alcohol Clin. Exp. Res. vol. 29, No. 6, 2005, pp. 999-1009.
Ma, TY; Boivin, MA; Ye, D; Pedram A; Said HM. Mechanism of TNF-α modulation of Caco-2 intestinal epithelial tight junction barrier: role of myosin light-chain kinase protein expression. Am. J. Physiol. Gastrointest. Liver Physiol. 288: G422-G430, 2005.
Ranaivo, HR; Carusio, N; Wangensteen, R; Ohlmann P; Liochot, C; Tesse, A; Chalupsky, K; Lobysheva, I; Haiesch, J; Watterson, DM; Andriantsitohaina, R. Protection Against Endotoxic Shock as a Consequence of Reduced Nitrosative Stress in MLCK210-Null Mice. The American Journal of Pathology, vol. 170, No. 2, Feb. 2007, pp. 439-446.
Tinsley, JH; Teasdale, NR; Yaun, SY. Myosin light chain phosphorylation and pulmonary endothelial cell hyperpermeability in burns. Am. J. Physiol. Lung Cell Mol. Physiol. 286: L841-L847, 2004.
Vernin, AD; Lazar, V; Torry, RJ. Labarrere, CA; Patterson, CE; Garcia, JGN. Expression of a Novel High Molecular-Weight Myosin Light Chain Kinase in Endothelium. Am. J. Respir. Cell Mol. Biol., vol. 19, pp. 758-766, 1998.
Schumacher, AM; Schavocky, JP; Velentza, AV; Mirzoeva S; Watterson, DM. A Calmodulin-Regulated Protein Kinase Linked to Neuron Survival Is a Substrate for the Calmodulin-Regulated Death-Associated Protein Kinase. Biochemistry, vol. 43, No. 25, 2004. pp. 8116-8124.
Behanna, HA; Watterson, DM; Ralay Ranaivo, H. Development of a novel bioavailable inhibitor of the calmodulin-regulated protein kinase MLCK: A lead compound that attenuates vascular leak. Biochemica et Biophysica Acta 1763 (2006) pp. 1266-1274.
Velentza, AV; Wainwright, MS; Zasadzki, M; Mirzoeva, S; Schumacher, AM; Haiech, J; Focia, PJ; Egli, M; Waterson, DM. An Aminopyridazine-Based Inhibitor of a Pro-apoptotic Protein Kinase Attenuates Hypoxia-Ischemia Induced Acute Brain Injury. Bioorganic & Medicinal Chemistry Letters 12, (2003), pp. 3465-3470.
Yuan, SY; Wu, MH; Usinova, EE; Guo, M; Tinsley, JH; De Lanerolle, P; Xu, W. Myosin Light Chain Phosphorylation in Neutrophil-Stimulated Coronary Microvascular Leakage. Circulation Research, 2202; 90; pp. 1214-1221; orginally published online May 2, 2002; DOI: 10.1161/01.RES.0000020402.73609.F1.
Bratcher, JM; Korelitz, BI. Toxicity of infliximab in the course of treatment of Crohn's disease. Expert Opinion on Drug Safety (2006), 5(1), 9-16. Publisher Ashley PUblications, Ltd. CAPULUS. (Abstract.).
Watterson, DM; Collinge, M; Lukas, TJ; Van Eldik, LJ; Birukov, KG; Stepanova, OV; Shirinsky, VP. Multiple gene products are produced from a novel protein kinase transcription region. FEBS Letters 373 (1995), pp. 217-220.
Zolotarevsky, Y; Hecht, G; Koutsouris, A; Gonzalez, DE; Quan, C; Tom, J; Mrsny, RJ; Turner, Jr. A Membrane-Permeant Peptide That Inhibits MLC Kinase Restores Barrier Function in in Vitro Models of Intestinal Disease. Gastroenterology 2002; vol. 123, No. 1, pp. 163-172.
Scott, KG-E; Meddings, JB; Kirk, DR; Lees-Miller, SP; Buret, AG. Intestinal Infection with Giardia ssp. Reduces Epithelial Barrier Function in a Myosin Light Chain Kinase-Dependent Fashion. Gastroenterology, vol. 123, No. 4, 2002, pp. 1179-1190.

(Continued)

*Primary Examiner* — Paul V. Ward
(74) *Attorney, Agent, or Firm* — Reinhart Boemer Van Deuren s.c.

(57) ABSTRACT

Pyridazinyl compounds, compositions and related methods of use.

16 Claims, 3 Drawing Sheets

OTHER PUBLICATIONS

Figure 1:
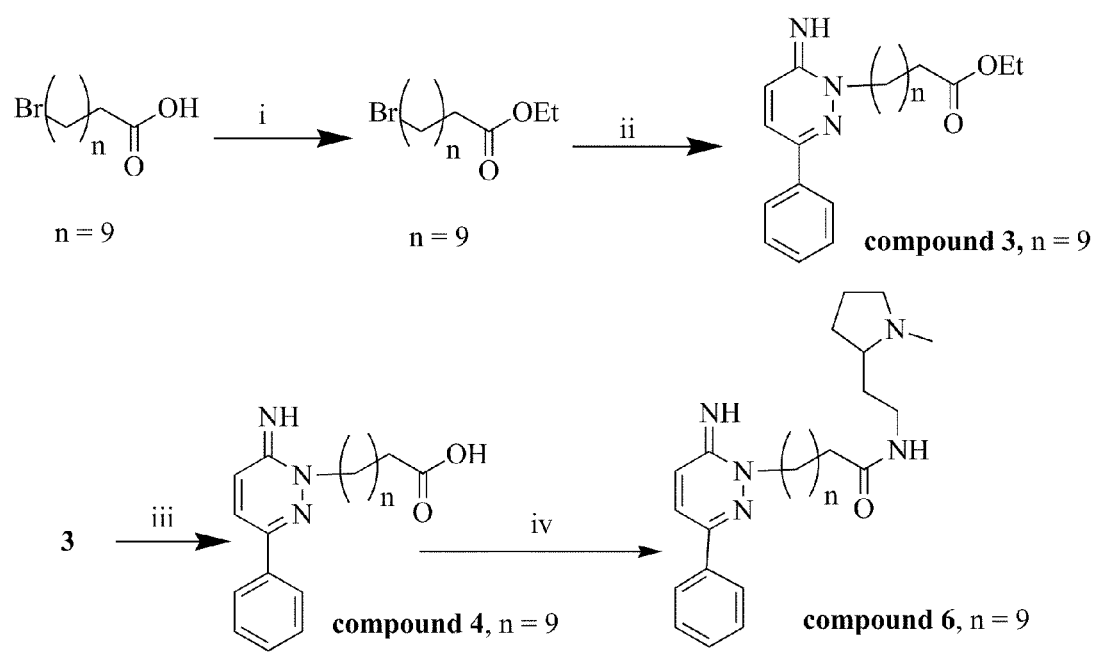

Clayburgh, DR; Barrett, TA; Tang, Y; Meddings, JB; Van Eldik, LJ; Watterson, DM; Clarke, LL; Mrsny, RJ; Turner, Jr. Epithelial myosin light chain kinase-dependent barrier dysfunction mediates T cell activation-induced diarrhea in vivo. The Journal of Clinical Investigation. vol. 115, No. 10, Oct. 2005, pp. 2702-2715.

Velentza, AV; Schumcher, AM; Weiss, C; Egli, M; Watterson, DM. A Protein Kinase Associated with Apoptosis and Tumor Suppression. The Journal of Biological Chemistry. vol. 276, No. 42, Issue of Oct. 19, 2001, pp. 38956-38965.

Demling, Robert H. The Burn Edema Process: Current Concepts. Journal of Burn Care & Rehabilitation. May/Jun. 2005, pp. 207-227.

Wermuth, C-G; Bourguignon, J-J; Schlewer, G; Gies, J-P; Schoenfelder, A; Melikian A; Bouchet, M-J; Chantreaux, D; Molimard, J-C; Heaulme, M; Chambon, JP; Biziere, K. Synthesis and Structure-Activity Relationships of a Series of Aminopyridazine Derivatives of γ-Aminobutyric Acid Acting as Selective GABA-A Antagonists. J. Med. Chem., 1987, vol. 30, No. 2, pp. 239-249.

Lukas, TJ; Mirzoeva, S; Slomczynska, U; Watterson, DM. Identification of Novel Classes of Protein Kinase Inhibitors Using Combinatorial Peptide Chemistry Based on Functional Genomics Knowledge. J. Med. Chem., 1999, vol. 42, No. 5, pp. 910-919.

Mirzoeva, S; Sawkar, A; Zasadzki, M; Guo, L; Vanentza AV; Dunlap V; Bourguignon, J-J; Ramstrom, H; Haiesch, J; Van Eldik, LJ; Watterson, DM. Discovery of a 3-Amino-6-phenyl-pyridazine Derivative as a New Synthetic Antineuroinflammatory Compound. J. Med. Chem., 2002, vol. 45, No. 3. pp. 563-566.

Mitsuhashi, T; Jones, WM. Stereospecific and Stereoselective Reactions. I. Preparation of Amines from Alcohols. J. Am. Chem. Soc. 94:2, Jan. 26, 1972, pp. 679-680.

Blair, SA; Kane SV; Clayburgh, DR; Turner, Jr. Epithelial myosin light chain kinase expression and activity are upregulated in inflammatory bowel disease. Laboratory Investigation (2006) 86, pp. 191-201.

Watterson, DM; Mirzoeva, S; Guo, L; Whyte, A; Bourguignon, J-J; Hibert, M; Haiesch, J; Van Eldik, LJ. Ligand modulation of glial activation: cell permeable, small molecule inhibitors of serine-threonine protein kinases can block induction of interleukin 1β and nitric oxide synthase II. Neurochemistry International 39 (2001) pp. 459-468.

Kaneko, K; Satoh, K; Masamune, A; Satoh, A; Shimesegawa, T. Myosin Light Chain Kinase Inhibitors Can Block Invasion and Adhesion of Human Pancreatic Cancer Cell Lines. Pancreas, vol. 24, No. 1, 2002, pp. 34-41.

Velentza, AV; Shumacher, AM; Watterson, DM. Structure, activity, regulation, and inhibitor discovery for a protein kinase associated with apoptosis and neuronal death. Pharmacology & Therapeutics, 93 (2002), pp. 217-224.

Mehta, D; Malik AB. Signaling Mechanisms Regulating Endothelial Permeability. Physiol. Rev.,vol. 86, Jan. 2006, pp. 279-367.

Wainwright, MS; Rossi, J; Schavocky, J; Crawford, S; Steinhorn, D; Venentza, AV; Zasadzki, M; Shirinsky, V; Jia, Y; Haiech, J; Van Eldik, LJ; Watterson, DM. Protein kinase involved in lung injury susceptibility: Evidence from enzyme isoform genetic knockout and in vivo inhibitor treatment. PNAS, May 13, 2003, vol. 100, No. 10, pp. 6233-6238.

Tohtong, R; Phattarasakul, K; Jiraviriyakul, A; Sutthiphongchai, T. Dependence of metastatic cancer cell invasion on MLCK-catalyzed phosphorylation of myosin regulatory light chain. Prostate Cancer and Prostatic Diseases (2003) 6, pp. 212-216.

Dreyfuss, D; Saumon, G. Ventilator-induced Lung Injury. Lessons from Experimental Studies. Am. J. Respir. Crit. Care Med., vol. 157, pp. 294-323, 1998.

Huang, Q; Xu, W; Ustinova, E; Wu, M; Childs, E; Hunter, F; Yuan, S. Myosin Light Chain Kinase-Dependent Microvascular Hyperpermeability in Thermal Injury. Shock, vol. 20, No. 4, pp. 363-368, 2003.

Reynoso, R; Perrin, RM; Breslin, JW; Daines, DA; Watson, KD; Watterson, DM; Hu, MH; Yuan, S. A Role for Long Chain Myosin Light Chain Kinase (MLCK-210) in Microvascular Hyperpermeability During Severe Burns. Shock, vol. 28, No. 5, pp. 589-595, 2007.

Maes, Buw; Lemiére, Glf; Dommisse, R; Augustyns, K; Haemers, A. A New Approach Towards the Synthesis of 3-Amino-6-(hetero)arylpyridazines Based on Palladium Catalyzed Cross-coupling Reactions. Tetrahedron 56 (2000) pp. 1777-1781.

Minamiya, Y; Nakagawa, T; Saito, H; Matsuzaki, I; Taguchi, K; Ito, M; Ogawa, J-I. Increased expression of myosin light chain kinase mRNA is related to metastasis in non-small cell lung cancer. Tumor Biology (2005), 26(3), pp. 156-157. CAPULUS. (Abstract.).

Yuan, S. Protein kinase signaling in the modulation of microvascular permeability. Vascular Pharmacology, 39 (2003), pp. 213-223.

Velentza, et al. Bioorg. & Med. Chem. Lett. (2003), 13(20),3465-3470.

Wainwright, et al., Proceedings of the National Academy of Sciences of the United States of America (2003), 100(10), 6233-6238.

* cited by examiner

MYOSIN LIGHT CHAIN KINASE INHIBITOR COMPOUNDS, COMPOSITIONS AND RELATED METHODS OF USE

This application is a divisional of and claims priority benefit from application Ser. No. 11/880,541 filed on Jul. 23, 2007, now U.S. Pat. No. 7,732,445 which claimed priority from provisional application Ser. No. 60/832,372 filed Jul. 21, 2006, the entirety of which is incorporated herein by reference.

This invention was made with government support under Grant No. NS 047586 awarded by the National Institutes of Health. The government has certain rights in the invention.

BACKGROUND OF THE INVENTION

The myosin II complex is involved in the regulation of eukaryotic cell structure and motility. Cell structure modulation in pathophysiology can result in modulation of gaps between cells in tissues, such as epithelial or endothelial layers that form tissue barriers, or in modulation of cell motility or chemotoxis, such as in the metastasis of tumor cells. Activation of the myosin II complex in physiology and pathophysiology requires phosphorylation of the myosin regulatory light chains (MLC) by myosin light chain kinase (MLCK), a highly specialized calcium/CaM regulated protein kinase that has MLC as its only physiological substrate. [T. J. Lukas, S. Mirzoeva and D. M. Watterson in (Van Eldik, L. J. and Watterson, D. M., eds.) Calmodulin and signal transduction, Academic Press 1998, pp. 65-168.] There is more than multiple MLCK enzymes, but the gene products that are most widely viewed as critical to disease and potential therapeutic intervention are the forms from one genetic locus. The forms are sometimes referred to as smooth muscle MLCK for the shorter form, due to its historical discovery first in smooth muscle tissue, and the long form or MLCK210 (in reference to the MW of 210,000 for the vertebrate protein, and often implied when the terms endothelial, epithelial, or non-muscle MLCK are used. [T. J. Lukas, S. Mirzoeva and D. M. Watterson in (Van Eldik, L. J. and Watterson, D. M., eds.) Calmodulin and signal transduction, Academic Press 1998, pp. 65-168.]. The predominant isoform of MLCK involved in tissue barrier regulation and tumor cell metastasis is the long form, or MLCK210. [A. D. Verin, V. Lazar, R. J. Tony, C. A. Labarrere, C. E. Patterson and J. G. Garcia, Am. J. Respir. Cell. Mol. Biol. 19 (1998) 758-66; D. M. Watterson, M. Collinge, T. J. Lukas, L. J. Van Eldik, K. G. Birukov, O. V. Stepanova and V. P. Shirinsky, FEBS Lett 373 (1995) 217-20.] A direct demonstration of the in vivo importance of MLCK210 in pathophysiology and its potential as a therapeutic target comes from the analysis of mice in which the gene for MLCK210 has been selectively knocked out, leaving the short form of MLCK intact. MLCK210 knockout (KO) mice, for example, are protected from inflammation linked tissue injury and death. The MLCK KO mice are protected in an animal model of acute immune-mediated diarrhea disease (e.g., Crohn's disease and episodic diarrhea associated with other diseses), in microvascular and lung injury associated with sepsis and microbial toxin induced injury, in neurologic outcomes from blood-brain barrier dysfunction associated with brain injury or disease, and in death from severe burn as a result of multi-organ failure. Congruent with the MLCK210 KO mouse results, wild type mice subjected to such tissue and microvascular injuries are protected by treatment with a selective MLCK inhibitor. In addition to providing a well established link between MLCK and tissue barrier functions that are points of susceptibility in disease progression in inflammation related injuries, these studies with MLCK210 KO mice and therapeutic doses of MLCK inhibitors established MLCK as a potential non-immune therapeutic target for certain inflammation related disorders. Similarly, therapeutic doses of MLCK inhibitors that inhibit tumor cell chemotaxis provides a link between the motility function of MLCK as a target in cancer and other disorders. As addressed elsewhere herein, it is understood in the art that MLCK affects tissue barrier function, cell motility and/or adhesion.

Currently, therapeutic approaches in diseases such as inflammatory bowel disorders or complications of severe bacterial infection are focused on the cytokines which are up-regulated and are among the active mediators of both endothelial and epithelial barrier dysfunction. Antibody therapies targeting these cytokines have been used, but they have limited stability, restricted utility due to their limited tissue distribution, and are expensive protein therapeutics with individual sets of safety problems. Non-protein therapies involving small molecules such as statins and glucocorticoids have some clinical effectiveness for inflammatory conditions, but are limited by their multiple biological effects and toxicity. In cancer chemotherapy, existing therapies are focused on cytotoxicity of the tumor and not on the motility related functions involved in metastasis. Accordingly, there is an unmet need for new and safe compounds, to optionally use as a co-therapy with other drugs or mechanical devices, to attenuate barrier and/or cell motility associated dysfunctions.

Based on the demonstrated protection from epithelial and endothelial barrier dysfunction afforded by inhibition of MLCK, by gene knockout or use of kinase inhibitors, one approach has been small molecule inhibitors of MLCK. However, currently available inhibitors are peptidic in nature or are expensive bioavailable small molecules for chemical biology research that are not readily amenable to further development. Accordingly, there remains an ongoing search in the art for a class of readily available, small molecule compounds, with corresponding system mechanism(s) of intervention, for MLCK inhibition.

SUMMARY OF THE INVENTION

In light of the foregoing, it is an object of the present invention to provide small-molecule, non-peptide therapeutic compounds, compositions and/or related methods for the use and treatment of tissue barrier dysfunction, tumor metatastasis, and related disease states, overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in its respects, to every aspect of this invention. As such, the following objects can be viewed in the alternative with respect with any one aspect of this invention.

It can be an object of the present invention to provide one or more compounds and related compositions for the treatment of tissue injury, barrier dysfunction and/or cell motility related disorder and/or one or more disease states pathophysiologically progressing therefrom.

It can be another object of this invention to provide a small molecule structural platform for variable compound design and/or therapeutic selectivity, from affordable starting materials and using straight-forward synthetic techniques.

It can be another object of the present invention alone or in conjunction with any one or more of the preceding objectives, to provide a range of compounds and related pharmaceutical compositions selected for inhibition of MLCK or closely related protein kinases, over other protein kinases such as but not limited to PKC and PKA.

Other objects, features, benefits and advantages of the present invention will be apparent from this summary and the following descriptions of certain embodiments, and will be readily apparent to those skilled in the art having knowledge of various small molecule therapeutic compounds and their rational design. Such objects, features, benefits and advantages will be apparent from the above as taken into conjunction with the accompanying examples, data, figures and all reasonable inferences to be drawn therefrom.

In part, this invention can be directed to a myosin light chain kinase inhibitor compound of a formula

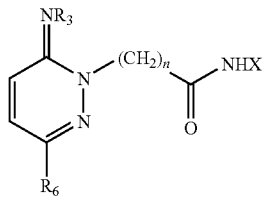

wherein $R_3$ can be selected from H and alkyl moieties; $R_6$ can be selected from H, halo, alkyl, aryl and heterocyclic moieties; n can be an integer ranging from about 8 to about 14; and X can be $(CH_2)_m Y$, where m can be an integer selected from 1 and 2 and Y can be selected from 5- and 6-member carbocyclic moieties, substituted 5- and 6-membered carbocyclic moieties, 5- and 6-membered heterocyclic moieties, and substituted 5- and 6-membered heterocyclic moieties; and salts of such a compound. In certain embodiments, m can be 2. Regardless, Y can be selected from substituted and unsubstituted 5-membered carbocylic, and substituted and unsubstituted 5-membered heterocyclic moieties. In certain such embodiments Y can be selected from pyrrolidinyl, pyrrolyl, pyrazolyl, imidazolyl and cyclopentyl moieties. As discussed elsewhere herein, one or more compounds of this invention can be embodied as a pharmaceutical composition, optionally comprising a pharmaceutically-acceptable carrier, such a composition as can, without limitation, be formulated for one of oral, intraperitoneal, intravenous and other modes of administration.

In part, this invention can also be directed to a method of inhibiting myosin light chain kinase activity. Such a method can comprise providing a medium comprising a myosin light chain kinase; and contacting such a medium with a compound of a formula

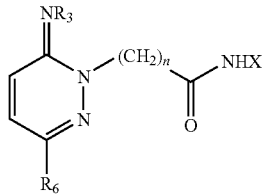

wherein $R_3$ can be selected from H and alkyl moieties; $R_6$ can be selected from H, halo, alkyl, aryl and heterocyclic moieties; n can be an integer ranging from about 8 to about 14; and X can be selected from $(CH_2)_m Y$ moieties where m can be an integer selected from 1 and 2 and Y can be selected from 5- and 6-member carbocyclic moieties, substituted 5- and 6-membered carbocyclic moieties, 5- and 6-membered heterocyclic moieties, and substituted 5- and 6-membered heterocyclic moieties, and salts thereof, such a compound in an amount sufficient to at least partially inhibit myosin light chain kinase activity. In certain embodiments, m and Y can be as discussed elsewhere herein. Regardless, such contact can be in vivo. Without limitation, such a method can comprise contacting at least one of epithelial and endothelial tissue exhibiting barrier dysfunction. For instance, one non-limiting embodiment can comprise contacting injured pulmonary tissue. Regardless, any one or more such compounds can be presented in a pharmaceutical composition.

In part, the present invention can also be directed to a method of treating progression of acute tissue injury. Such a method can comprise providing at least one of epithelial and endothelial tissue with barrier dysfunction; and contacting such a tissue with a compound of a formula

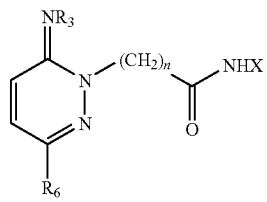

wherein $R_3$ can be selected from H and alkyl moieties; $R_6$ can be selected from H, halo, alkyl, aryl and heterocyclic moieties; n can be an integer ranging from about 8 to about 14; and X can be selected from $(CH_2)_m Y$ moieties where m can be an integer selected from 1 and 2 and Y can be selected from 5- and 6-member carbocyclic moieties, substituted 5- and 6-membered carbocyclic moieties, 5- and 6-membered heterocyclic moieties, and substituted 5- and 6-membered heterocyclic moieties, and salts thereof, such compound(s) in a therapeutically sufficient or effective amount. In certain embodiments, such compounds can be as discussed elsewhere herein, with respect to one or more structural variables. Regardless, such a method can comprise in vivo contact. In certain such embodiments, such a compound can be provided in an amount selective for MLCK inhibition over inhibition of at least one of DAPK, PKC and PKA. Optionally, such efficacy and selectivity can be confirmed against MLCK210 (KO) mice.

In part, this invention can also be directed to a method of using amide moiety structure for selective kinase inhibition. Such a method can comprise providing a pyridazinylalkaneamide compound of a formula

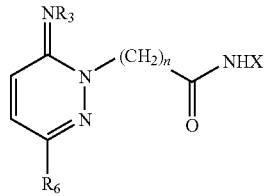

wherein $R_3$ can be selected from H and alkyl moieties; $R_6$ can be selected from H, halo, alkyl, aryl and heterocyclic moieties; n can be an integer ranging from about 10 to about 14; and X can be selected from $(CH_2)_m Y$ moieties where m can be an integer selected from 1 and 2 and Y can be selected from 5- and 6-member carbocyclic moieties, substituted 5- and 6-membered carbocyclic moieties, 5- and 6-membered heterocyclic moieties, and substituted 5- and 6-membered heterocyclic moieties, and salts thereof; and contacting such compound with a medium comprising a myosin light chain kinase, such a compound in an amount sufficient to at least partially inhibit said kinase activity, and such an X moiety providing said compound inhibition activity selective over at least one of death-associated protein kinase, protein kinase A and protein kinase C. In certain such embodiments, myosin light chain kinase inhibition selectivity can be varied with said X moiety. Regardless, such a compound can comprise an X moiety providing, at least in part, such a compound with an aqueous solubility of log S about ≦−3. In certain such embodiments, X can be selected from

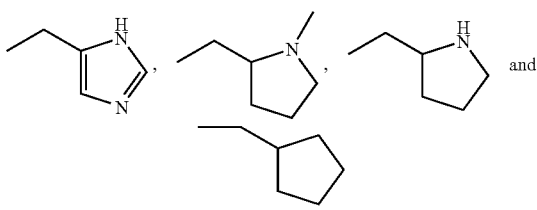

moieties.

In part, this invention can also be directed to a myosin light chain kinase inhibitor compound of a formula

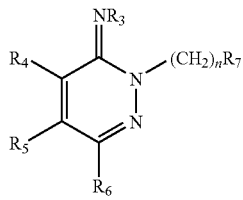

wherein $R_3$ can be selected from H and alkyl moieties; $R_4$ can be selected from H, alkyl, substituted alkyl, phenyl and substituted phenyl moieties; $R_5$ can be selected from H and alkyl moieties; $R_6$ can be selected from phenyl, substituted phenyl and halo moieties; and $R_7$ can be selected from NHC(O)X and C(O)NHX, where X can be $(CH_2)_mY$, and m can be an integer selected from 0 to about 3, and Y can be selected from 5- and 6-membered carbocyclic moieties, substituted 5- and 6-membered carbocyclic moieties, 5- and 6-membered heterocyclic moieties and substituted 5- and 6-membered heterocyclic moieties; and salts thereof. In certain embodiments, $R_7$ can be C(O)NHX, m can be 2 and Y can be selected from 5-membered carbocyclic and heterocyclic moieties. In certain such embodiments, Y can be selected from pyrrolidinyl, pyrrolyl, pyrazolyl, imidazolyl and cyclopentyl moieties. Such a compound(s) can be presented as a pharmaceutical composition, optionally formulated for oral, intraperitoneal, intravenous and other modes of administration, as can be employed to contact a medium comprising a myosin light chain kinase.

In part, this invention can also be directed to a method of treating a disease state affecting cell motility. Such a method can comprise providing a subject presenting a disease state comprising a disorder of cell motility; and administering said subject a therapeutically-effective amount of a compound of a formula

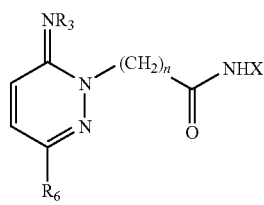

wherein $R_3$ can be selected from H and alkyl moieties; $R_6$ can be selected from H, halo, alkyl, aryl and heterocyclic moieties; n can be an integer ranging from about 8 to about 14; and X can be $(CH_2)_mY$, where m can be an integer selected from 1 and 2 and Y can be selected from 5- and 6-member carbocyclic moieties, substituted 5- and 6-membered carbocyclic moieties, 5- and 6-membered heterocyclic moieties, and substituted 5- and 6-membered heterocyclic moieties, and salts thereof. In certain embodiments, with respect to one or more structural variables, such a compound can be as discussed above. Regardless, without limitation, such a disease state can comprise a cancer, a neurological disorder, or a disease state selected from intestinal, cardiovascular and lung disorders.

The compounds of the present invention, as can be used in conjunction with compositions and/or methods of the sort described herein, can suitably comprise, consist of or consist essentially of any of the moieties or components or substituents thereof discussed herein. Each such compound or moiety/substituent/component thereof is compositionally distinguishable, characteristically contrasted and can be practiced in conjunction with the present invention separate and apart from another. Accordingly, it should also be understood that the inventive compounds, compositions and/or methods, as illustratively disclosed herein, can be practiced or utilized in the absence of any one compound or moiety/component/substituent thereof which may or may not be disclosed, referenced or inferred herein, the absence of which may or may not be specifically disclosed, referenced or inferred herein.

DETAILED DESCRIPTION OF THE DRAWINGS

FIG. 1: Synthetic scheme for production of compound 6.
i) EtOH, HCl, rt, 48 h; ii) DMF, 3-amino-6-phenyl pyridazine, 80° C., 12 h; iii) AcOH, HCl, reflux, 5 h; iv) HBTU/HOAT, DIEA, 2-(1-methylpyrrolidin-2-yl)ethanamine, NMP, microwave, Power 200 W for 15 min at 55° C. and then 300 W for 20 min at 60° C.

FIGS. 2A-B: Compound 6 protects mice from bacterial toxin-induced pulmonary vascular leak.

A) Therapy with MLCK inhibitor compound 6 protects mice from pulmonary vascular leak as determined by decreased levels of Evans blue dye appearing in the lungs. Mice were administered Evans blue dye and exposed to bacterial toxin lipopolysaccharide (LPS) or saline (Sal) by intraperitoneal (i.p.) injection. A subset of the mice exposed to LPS were also injected i.p. with MLCK inhibitor compound 6. The relative levels of dye appearing in lung tissue 24 h later were then determined for all mice. Mice exposed to LPS (10 mg/kg) and receiving 5 mg/kg of the compound 6 (LPS+cmpd6) exhibit lung levels of dye comparable to that seen with control mice not exposed to LPS and administered only saline (Sal). The protection afforded mice by compound 6 therapy is reflected in the significantly lower (*$p<0.05$) levels of dye in the lungs of these mice compared to those not receiving therapy (LPS).

B) The protection afforded by therapy with compound 6 (panel A) is comparable to the protection seen by genetic knockout (KO) of the target MLCK. In a parallel control experiment, mice were administered Evans blue dye, exposed to LPS or saline, and lung tissue examined 24 hr later, as in panel A. MLCK210 KO mice are protected from LPS-induced vascular leak (KO+LPS) to levels comparable to saline treated control wild type mice (Sal). The protection afforded mice by genetic KO of the target MLCK is reflected in the significantly lower (***$p<0.001$) levels of dye in the lungs of these mice compared to those not receiving therapy (LPS). Data shown represent the mean±SEM for 4-5 mice in each group. Results were analyzed by one way-ANOVA followed by a Neuman-Keuls post-hoc test.

Figure 3:
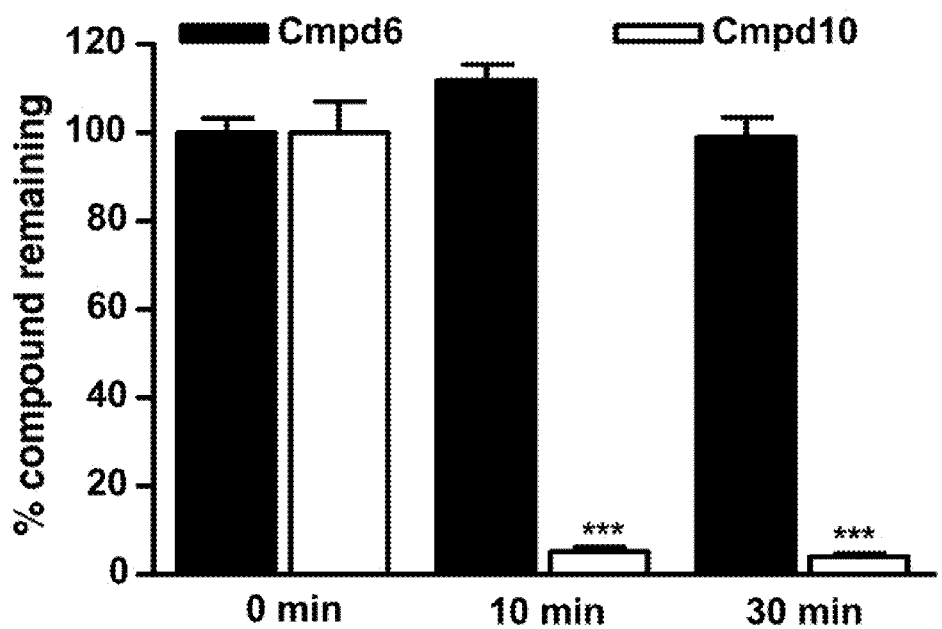

FIG. 3: Compound 6 exhibits in vitro metabolic stability in screens with human liver microsomes. The amount of compound 6 and its carbocycle analog compound 10 remaining after 10 and 30 min incubations with commercially available human liver microsomes was determined by HPLC analysis. The majority of compound 6 (filled bar) remains after 10 and 30 min incubation times, in contrast to the carbocycle compound 10 (open bar). The levels of compound 10 are significantly different (***$p<0.001$) at 10 and 30 min compared to zero min. Data shown represent the mean±SEM of triplicate samples at each time point. Results are analyzed by one way-ANOVA followed by a Neuman-Keuls post-hoc test.

DETAILED DISCUSSION OF CERTAIN EMBODIMENTS

Illustrating certain non-limiting aspects and embodiments of this invention, the successful development of representative compound 6 targeting MLCK demonstrates the feasibility for pursuit of a new class of therapeutics that address a major unmet medical need across multiple areas of disease and injury. The precedent described here for this bioavailable MLCK inhibitor also supports the use of integrative chemical biology reagents for in vivo dissection of protein kinase mediated, calcium signal transduction pathways.

Compound 6 is selective for MLCK compared to closely related protein kinases. For example, with reference to Table 1, below, it is over 76 times more selective for MLCK versus DAPK, another calcium/CaM regulated protein that has a catalytic domain structurally similar to that of MLCK, similar peptide substrate preferences, and the novel ability to mimic MLCK's unique ability to phosphorylate myosin light chains at Ser 9. The compound is also selective for MLCK over other protein kinases, such as PKC and PKA, that are involved in potentially convergent signaling pathways or in vivo crosstalk with MLCK regulated processes. The selectivity of the present inhibitor compounds was accomplished by diversification of an N2-alkylated aminopyridazine scaffold via facile amination reactions. It was observed that various 5-membered aliphatic amines could be incorporated into the structure (e.g., compounds 6, 9, 10) without a major loss of MLCK inhibitory activity. However, the placement of the amines in relation to the pyridazine scaffold appears to be a consideration, as shortening the carbon linker can affect inhibitory activity and/or selectivity (compound 7). These results suggest that the amine portion of these bi-headed molecules interacts with regions of protein kinase catalytic domains involved in peptide substrate binding. This implies that future compound refinement might allow selective targeting of inhibitor interactions to the peptide substrate binding region of MLCK.

Compound 6 is stable in human liver microsome (HLM) screens for potential human first pass metabolic susceptibility, a common cause of in vivo efficacy failure or complications in human therapeutic development. The predominant human cytochrome P450 isoforms that are involved in the metabolism of the majority of currently used drugs are a major component of the metabolic activity in these calibrated HLMs. This includes P450 isoform CYP2D6, the major source of functional polymorphisms in human first pass metabolism of drugs. The fact that compound 6 is stable in these HLM assays suggests that there will be less individual variance in metabolism of compound 6 or analogs thereof, and less potential for drug-drug interactions. The results also raise the possibility for enhancing therapeutic efficacy in future drug development by refining either pharmacokinetics or pharmacodynamics of such compounds. Syntheses of the compounds of this invention, as illustrated by compound 6, proceed with good synthetic yields—a feature attractive from a potential production perspective, using commercially available and inexpensive starting materials. Therefore, the biological results, synthetic scheme, structural diversity and the computed molecular properties make the present compounds compatible with future development and formulation as a therapeutic for major unmet medical needs involving tissue barrier dysfunction, especially in critical care medicine or intestinal disorders, clinical areas that are lacking robust and safe small molecule therapies.

Endothelial and epithelial barrier dysfunctions are key elements in the pathophysiology of diverse diseases in which targeting MLCK is a viable approach based on the accumulating body of evidence, whether using bioavailable inhibitors in animal models of disease or MLCK210 KO mice in models of disease relevant injuries. As shown here, MLCK can be a potential target for treatment of pathologies that involve endothelial barrier dysfunction as an underlying cause. The human disease counterparts are diverse, including sepsis associated organ failure, pulmonary hypertension related tissue injury, and complications of severe burn. For example, thermal injury induces massive tissue edema in patients. MLCK dependent pathways have been implicated in this pathophysiology progression and inhibition of MLCK decreased the leak induced by the thermal injury. [Q. Huang, W. Xu, E. Ustinova, M. Wu, E. Childs, F. Hunter and S. Yuan, Shock 20 (2003) 363-8; J. H. Tinsley, N. R. Teasdale and S. Y. Yuan, Am. J. Physiol Lung Cell Mol Physiol 286 (2004) L841-7.] MLCK inhibitors also have a potential role in treatment of epithelial barrier dysfunction related disorders, such as inflammatory bowel disease. MLCK is involved in the regulation of tight junctions in response to various pathological stimuli [D. Mehta and A. B. Malik, Physiol. Rev. 86 (2006) 279-367], and MLCK expression and enzymatic activity are increased in colon biopsies from patients with inflammatory bowel disease. [S. A. Blair, S. V. Kane, D. R. Clayburgh and J. R. Turner, Lab. Invest. 86 (2006) 191-201.] Further, treatment with MLCK inhibitors in animal models or deletion of MLCK210 restores intestinal barrier function in response to diverse pathological stimuli. [D. R. Clayburgh, T. A. Barrett, Y. Tang, J. B. Meddings, L. J. Van Eldik, D. M. Watterson, L. L. Clarke, R. J. Mrsny and J. R. Turner, J. Clin. Invest. 115 (2005) 2702-15; Y. Zolotarevsky, G. Hecht, A. Koutsouris, D. E. Gonzalez, C. Quan, J. Tom, R. J. Mrsny and J. R. Turner, Gastroenterology 123 (2002) 163-72; T. Y. Ma, M. A. Boivin, D. Ye, A. Pedram and H. M. Said, Am. J. Physiol Gastrointest Liver Physiol. 288 (2005) G422-30.] This accumulating body of disease-relevant evidence supports use of the compounds of this invention for the prevention or treatment of diseases and injuries associated with tissue barrier dysfunctions.

MLCK is also important in cell motility through its effects on the actomyosin cytoskeletal system. This function of MLCK has important implications in the field of cancer therapeutics. Tumor cell invasion and metastasis are processes that involve changes in cell motility and adhesion that lead to detachment of cells from the primary tumor and subsequent invasion of tumor cells into adjacent blood vessels or tissues. MLCK is important in these cellular adhesive and motility changes, and dysregulation of MLCK levels or activity has been seen in a variety of metastatic cancers or other disorders involving motility and metastasis. For example, MLCK expression in non-small cell lung cancer is higher in patients who showed disease recurrence and distant metastasis than in those who did not. Further, treatment of human pancreatic cancer cells, an adenocarcinoma cell line, or a metastatic prostate cancer cell line reduced chemotaxis and invasiveness without affecting cell growth or viability. These and other recent findings suggest that MLCK inhibitor drugs might be effective as a cancer therapeutic or as a co-therapy with other cancer drugs.

Evidence to date supports therapeutic use of a selective MLCK inhibitor of this invention with any disorder where tissue barrier dysfunction or changes in cell motility are part of the disease mechanism or progression of pathophysiology. These include a large number of diseases in a variety of categories, including but not limited to skin disorders: including ichthyosis vulgaris, atopic dermatitis, psoriasis, eczema, allergic skin disease, and hypersensitivity reactions; intestinal disorders: including inflammatory bowel disease, Crohn's disease, ulcers, bacterial infections hemorrhagic shock, diarrhea, colitis, viral and alcoholic liver disease, pancreatitis; lung disorders: including acute lung injury after infection, mechanical ventilation-induced injury, sepsis, thrombin-induced lung injury, lung injury after reperfusion; interstitial cystitis of the bladder; coronary disease after ischemia-reperfusion injury, flow-induced injury, aortic aneurysm, hypertension; burn-induced injury; chorioretinal vascular disease; neurologic disorders: including multiple sclerosis, Alzheimer's disease, vascular dementia, traumatic brain injury, ALS, Parkinson's disease, stroke, meningoencephalitis, cerebral hemorrhage, Guillain-Barre syndrome, vasogenic brain edema, hypoxia-induced injury and blood brain barrier compromise after ethanol toxicity; and cancers, including metastatic cancers such as non-small cell lung cancers, pancreatic cancer, adenocarcinoma and prostate cancer. See, e.g., Behanna H A, Watterson D M and Ralay Ranaivo H (2006) Development of a novel bioavailable inhibitor of the calmodulin-regulated protein kinase MLCK: a lead compound that attenuates vascular leak. Biochim Biophys Acta 1763: 1266-1274; Behanna H A, Bergan R and Watterson D M (2007), unpublished observations; Bratcher J M and Korelitz B I (2006) Toxicity of infliximab in the course of Crohn's disease. Expert Opin Drug Saf 5: 9-16; Clayburgh D R, Shen L and Turner J R (2004) A porous defense: the leaky epithelial barrier in intestinal disease. Lab Invest 84: 282-291; Clayburgh D R, Barrett T A, Tang Y, Meddings J B, Van Eldik L J, Watterson D M, Clarke L L, Mrsny R J and Turner J R (2005) Epithelial myosin light chain kinase-dependent barrier dysfunction mediates T cell activation-induced diarrhea in vivo. J Clin Invest 115: 2702-2715; Demling R H (2005) The burn edema process: current concepts. J Burn Care Rehabil 26: 207-227; Dreyfuss D and Saumon G (1998) Ventilator-induced lung injury: lessons from experimental studies. Am J Respir Crit. Care Med 157: 294-323; Haorah J, Heilman D, Knipe B, Chrastil J, Leibhart J, Ghorpade A, Miller D W and Persidsky Y (2005) Ethanol-induced activation of myosin light chain kinase leads to dysfunction of tight junctions and blood-brain barrier compromise. Alcohol Clin Exp Res 29: 999-1009; Huang Q, Xu W, Ustinova E, Wu M, Childs E, Hunter F and Yuan S (2003) Myosin light chain kinase-dependent microvascular hyperpermeability in thermal injury. Shock 20: 363-368; Kaneko K, Satoh K, Masamune A, Satoh A and Shimosegawa T (2002) Myosin light chain kinase inhibitors can block invasion and adhesion of human pancreatic cancer cell lines. Pancreas 24: 34-41; Ma T Y, Boivin M A, Ye D, Pedram A and Said H M (2005) Mechanism of TNFα modulation of Caco-2 intestinal epithelial tight junction barrier: role of myosin light-chain kinase protein expression. Am J Physiol Gastrointest Liver Physiol 288: G422-G430; Minamiya Y, Nakagawa T, Saito H, Matsuzaki I, Taguchi K, Ito M and Ogawa J (2005) Increased expression of myosin light chain kinase mRNA is related to metastasis in non-small cell lung cancer. Tumour Biol 26: 153-157; Ralay Ranaivo H, Carusio N, Wangensteen R, Ohlmann P, Loichot C, Tesse A, Chalupsky K, Lobysheva I, Haiech J, Watterson D M and Andriantsitohaina R (2007) Protection against endotoxic shock as a consequence of reduced nitrosative stress in MLCK210-null mice. Am J Pathol 170:439-446; Reynoso R, Perrin R M, Breslin J W, Daines D A, Watson K D, Watterson D M, Wu M H and Yuan S (2007) A role for long chain myosin light chain kinase (MLCK-210) in microvascular hyperpermeability during severe burns. Shock, June 14 epub; Rossi J, Bayram M, Udelson J E, Lloyd-Jones D, Adams K F, Oconnor C M, Stough W G, Ouyang J, Shin D D, Orlandi C and Gheorghiade M (2007) Improvement in hyponatremia during hospitalization for worsening heart failure is associated with improved outcomes: insights from the Acute and Chronic Therapeutic Impact of a Vasopressin Antagonist in Chronic Heart Failure (ACTIV in CHF) trial. Acute Card Care 9:82-86; Scott K G, Meddings J B, Kirk D R, Lees-Miller S P and Buret A G (2002) Intestinal infection with *Giardia* spp. reduces epithelial barrier function in a myosin light chain kinase-dependent fashion. Gastroenterology 123: 1179-1190; Tohtong R, Phattarasakul K, Jiraviriyakul A and Sutthiphongchai T (2003) Dependence of metastatic cancer cell invasion on MLCK-catalyzed phosphorylation of myosin regulatory light chain. Prostate Cancer Prostatic Dis 6: 212-216; Yuan S Y (2002) Protein kinase signaling in the modulation of microvascular permeability. Vascul Pharmacol 39: 213-223; Yuan S Y, Wu M H, Ustinova E E, Guo M, Tinsley J H, De Lanerolle P and Xu W (2002) Myosin light chain phosphorylation in neutrophil-stimulated coronary microvascular leakage. Circ Res 90: 1214-1221; Zolotarevsky Y, Hecht G, Koutsouris A, Gonzalez D E, Quan C, Tom J, Mrsny R J and Turner J R (2002) A membrane-permeant peptide that inhibits MLC kinase restores barrier function in in vitro models of intestinal disease. Gastroenterology 123 (2002) 163-172.

More generally, for purposes of the present compounds, compositions and/or methods, the following expression(s) and word(s), unless otherwise indicated, will be understood in light of the following and as would further understood by those skilled in the art:

As used herein, the terms "administering" and "administration" refer to a process by which a compound or composition, whether or not therapeutically-effective, is delivered to a subject for a treatment purpose or another use as described herein, taking into consideration the site and/or method of administration, dosage, and other factors known to or understood by those skilled in the art. Such compounds and/or related compositions can be administered alone or together, whether or not concurrently or simultaneously, with one or more other compounds, compositions and/or therapeutic agents. Such co-administering or co-administration would be as understood by those skilled in the art with respect to the formulations, dosages, modes and/or routes of such administration or co-administration.

As used herein, the term "treating" refers to reversing, alleviating, attenuating, affecting, or inhibiting the progress of a disease, disease state and/or one or more symptoms relating to such a disease or disease state. Depending upon the condition of a subject, the term also refers to preventing a disease and includes preventing the onset of a disease while preventing symptoms associated with a disease. The term can also refer to reducing the severity of a disease or symptoms associated with such a disease or disease state prior to affliction with such a disease/disease state.

The term "contacting" refers to bringing a compound or composition of this invention together with a subject and/or a cellular tissue thereof or an in vitro or in vivo medium, such a subject, tissue and/or medium as can comprise a kinase, such a compound or composition can affect kinase activity therein.

As used herein, the term "therapeutically-effective" relates to the amount or dose of a compound or composition comprising such a compound that will lead to one or more desired effects. A therapeutically-effective amount of such a compound or composition can vary or can be administered over time.

As used herein, the term "alkyl" refers to a monovalent, saturated hydrocarbon radical or moiety which may be linear or branched. Without limitation, an alkyl radical/moiety generally comprises from about 1 to about 20 carbon atoms, and can be substituted with a range of substituents including but not limited to halo, hydroxy, cyano, nitro, amino and/or other substituents as would be understood by those in the art. Substituents on such an alkyl group may themselves be substituted.

As used herein, the term "carbocyclic" refers to radicals or moieties derived from a saturated or unsaturated, substituted or unsubstituted 5 to about 14-member ring configuration of carbon atoms. Examples of carbocyclic radicals/moieties include but are not limited to cycloalkyl, cycloalkenyl, and aryl, in particular phenyl. Ring substituents can include alkyl, substituted alkyl, aryl and other substituents of the sort discussed herein.

As used herein, the term "aryl", alone or in combination, refers to a carbocyclic aromatic system containing 1, 2 or 3 rings either bonded together in a pendant manner or as may be fused. Without limitation, such aryl radicals or moieties can be substituted or unsubstituted as otherwise discussed herein. Non-limiting representative aryl radicals/moieties include phenyl, benzyl, naphthyl and indenyl.

As used herein, the term "heterocyclic" refers to radicals or moieties derived from a saturated or unstaturated, substituted or unsubstituted, 3 to about 14-membered ring configuration having at least 1 ring-forming atom other than carbon, such heteroatom(s) can be selected from, without limitation, nitrogen, sulfur and oxygen. A heterocyclic radical/moiety may comprise 1, 2 or 3 rings, either pendant to one another or fused. Without limitation, representative saturated heterocyclic radicals/moieties include piperidinyl and thiazolidinyl radicals. Likewise, representative examples of unstaturated heterocyclic radicals/moieties include, without limitation, dihydropyranyl and pyrazolinyl. Substituents, whether or not on a heteroatom, can include those of the sort discussed herein, such substituents including but not limited to alkyl, substituted alkyl, aryl and substituted aryl substituents.

The compounds of this invention may contain a basic functional group and are, thus, capable of forming pharmaceutically-acceptable salts with pharmaceutically-acceptable acids. The term "pharmaceutically-acceptable salts" refers to the relatively non-toxic, inorganic and organic acid addition salts of such compounds. These salts can be prepared by reacting such a compound with a suitable acid. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

Whether or not present as a salt, a compound of this invention can be present as a tautomer, a hydrate and/or solvate of such a compound. If such a compound has an asymmetric center, a range of available enantiomers, diasteriomers and other stereoisometric forms are contemplated within the scope of this invention. Likewise, the present invention includes derivatives of any such compound; that is the term "derivative" refers to a chemically-modified compound wherein such a chemical modification is with respect to a functional group of or on such a compound.

To treat an animal/subject disease state or condition, in accordance with this invention, an effective amount of one or more of the present compounds, or a pharmaceutically-acceptable salt thereof, is administered. Effective dosage forms, modes of administration and dosage amounts may be determined empirically, and making such determinations is within the skill of the art. It is understood by those skilled in the art that the dosage amount will vary with the activity of the particular compound employed, the severity of the condition, the route of administration, the rate of excretion of the compound, the duration of the treatment, the identity of any other drugs being administered to the animal/subject, the age, size and species of the animal, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of such a compound, or a pharmaceutically-acceptable salt thereof, maybe administered as two, three, four, five, six or more sub-doses, administered separately at appropriate intervals throughout the day. Treatment according to the invention, includes mitigation or attenuation, as well as elimination, of the condition. Animals treatable according to the invention include mammals. Mammals treatable according to the invention include dogs, cats, other domestic animals, and humans.

Compounds or composition of this invention may be administered to an animal/patient for therapy by any suitable route of administration, including orally, nasally, rectally, intravaginally, parenterally, intracisternally and topically, as by powders, ointments or drops, including buccally and sublingually.

While it is possible for the active ingredient(s) (one or more compounds of this invention and/or pharmaceutically-acceptable salts thereof, alone or in combination or sequence with another therapeutic agent) to be administered alone, it is possible to administer the active ingredient(s) as a pharmaceutical formulation (composition). The pharmaceutical compositions of the invention can comprise the active ingredient(s) in admixture with one or more pharmaceutically-acceptable carriers and, optionally, with one or more other compounds, drugs or other materials. Each carrier should be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly (anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multidose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

EXAMPLES OF THE INVENTION

Chemicals were purchased from Aldrich (Milwaukee, Wis.) or VWR International, and used as received. All solvents were used as received unless stated otherwise. All water used was Milli-Q water obtained using a Biocel A10 water purification system from Millipore Corporation (Bedford, Mass.), unless stated otherwise. Microwave irradiation was carried out using the CEM Discover microwave synthesis system (Matthews, N.C.).

Progression of synthetic reactions was monitored by analytical HPLC on a Rainin Instruments HPLC using a Supelco C18 reverse phase column (250×4.6 mm, 5 µm) at a flow rate of 1.0 ml/min and monitored by UV absorption at 260 nm. The mobile phase consisted of 0.1% (v/v) formic acid (Fluka) in water as reagent A and 0.08% formic acid/water in 80% acetonitrile (Burdick & Jackson) as reagent B.

All compounds were synthesized using a variation of previously described synthetic scheme. [S. Mirzoeva, A. Sawkar, M. Zasadzki, L. Guo, A. V. Velentza, V. Dunlap, J. J Bourguignon, H. Ramstrom, J. Haiech, L. J. Van Eldik and D. M. Watterson, J. Med. Chem. 45 (2002) 563-6; A. V. Velentza, M. S. Wainwright, M. Zasadzki, S. Mirzoeva, A. M. Schumacher, J. Haiech, P. J. Focia, M. Egli and D. M. Watterson, Bioorg. Med. Chem. Lett. 13 (2003) 3465-70.] Details of synthesis for each compound made as part of this study are summarized under Results.

Purity of compounds and bioanalytical analyses were determined on a Dionex HPLC system (Dionex, Sunnyvale, Calif.) using a Phenomenex (Torrance, Calif.) Luna C18 column (250×2.0 mm; 5 nm) and guard column with a flow rate of 0.2 ml/min. The system consisted of a Dionex P680 pump, ASI-100 auto-sampler, and UVD170U ultraviolet detector. Reagents A and B were as described above, unless otherwise stated. For determination of compound purity, the gradient consisted of a linear change from 0 to 100% of reagent B over 30 minutes. UV absorption was monitored at four wavelengths (215, 230, 260 and 300 nm) with the 260 nm trace being reported. The approximate upper and lower limits of detection for the 3-amino-6-arylpyridazine analogs are, respectfully, 2 µg and 0.030 µg. For purity analysis by HPLC, 0.5 µg of each compound was analyzed.

All compounds were characterized minimally by electrospray mass spectroscopy (ESI) and HPLC. Compounds used for metabolic stability and in vivo studies were additionally characterized by high resolution mass spectra (HRMS) and ¹HNMR. NMR spectra were acquired on a Varian Inova 500 MHz spectrometer at room temperature. ESI mass spectra were collected on a Micromass Quattro I I Triple Quadrupole HPLC/MS/MS Mass Spectrometer. HRMS spectra were obtained on a VG70-250SE mass spectrometer. Melting point data for compound 6 (119° C.) were acquired on a Büchi Melting Point B-540 (Flawil, Switzerland).

Example 1

Screening for In Vitro Inhibition Activity

MLCK inhibitory activity screens were done by incubation with 20 µM peptide substrate (KKRPQRATSNVFAM-NH$_2$), 200 µM ATP and [$^{32}$P]-ATP (2.5 µCi per reaction) in assay buffer (50 mM HEPES, pH 7.5 with KOH, 5 mM MgCl$_2$, 0.15 M KCl, 0.015 M NaCl, 1 mM DTT) with 0.1 mM CaCl$_2$ and 1 µM calmodulin (New England Biolabs, Mass.). [T. J. Lukas, S. Mirzoeva, U. Slomczynska and D. M. Watterson, J. Med. Chem. 42 (1999) 910-9.]Reactions were initiated by addition of MLCK protein and incubated for 20 min at 25° C. Reactions were spotted onto P-81 paper (Whatman, Clifton, N.J.), washed with 75 mM H$_3$PO$_4$ and 95% EtOH, and quantified by scintillation counting in EcoScintO (National Diagnostics, Atlanta, Ga.). Testing of compounds for kinase inhibitory activity against the structurally and functionally related kinases death-associated protein kinase (DAPK) and the signal transduction pathway relevant kinases protein kinase A (PKA) and protein kinase C(PKC) was performed as described by using the corresponding peptide substrates and assay conditions. [S. Mirzoeva, A. Sawkar, M. Zasadzki, L. Guo, A. V. Velentza, V. Dunlap, J. J. Bourguignon, H. Ramstrom, J. Haiech, L. J. Van Eldik and D. M. Watterson, J. Med. Chem. 45 (2002) 563-6; A. M. Schumacher, J. P. Schavocky, A. V. Velentza, S. Mirzoeva and D. M. Watterson, Biochemistry 43 (2004) 8116-24; A. V. Velentza, A. M. Schumacher and D. M. Watterson, Pharmacol Ther 93 (2002) 217-24; A. V. Velentza, A. M. Schumacher, C. Weiss, M. Egli and D. M. Watterson, J. Biol. Chem. 276 (2001) 38956-65; D. M. Watterson, S. Mirzoeva, L. Guo, A. Whyte, J. J. Bourguignon, M. Hibert, J. Haiech and L. J. Van Eldik, Neurochem Int. 39 (2001) 459-68.]

Example 2

Screening for In Vivo Function

Adult (20-30 g) female C57B1/6 mice were obtained from a commercial vendor (Harlan, Indianapolis, Ind.). The generation and characterization of the MLCK210 KO mouse strain was previously described. [M. S. Wainwright, J. Rossi, J. Schavocky, S. Crawford, D. Steinhorn, A. V. Velentza, M. Zasadzki, V. Shirinsky, Y. Jia, J. Haiech, L. J. Van Eldik and D. M. Watterson, Proc. Natl. Acad. Sci. USA 100 (2003) 6233-8.] All animal procedures were performed in accordance with relevant National Institutes of Health guidelines and approved by the Institutional Animal Care and Use Committee of Northwestern University.

Example 3

Measurement of Bacterial Toxin-Induced Pulmonary Vascular Leak

Pulmonary vascular leak after injurious endotoxin exposure was examined essentially as previously described, above, except using the increase in Evans blue dye in the lung as a quantitative end point. Treatments with lipopolysaccharide (LPS, from *S. typhimurium*, Sigma, St. Louis, Mo.), Evans blue dye (Alfa Aesar, Ward Hill, Mass.) or compound were all done by intraperitoneal (i.p) administration. Mice were administered either an injurious concentration (10 mg/kg) of LPS or saline as part of the control group. A subset of mice (drug treated) was administered MLCK inhibitor (5 mg/kg). Animals were euthanized with 200 mg/kg of pentobarbital 24 h after treatments, and blood was drawn by intracardiac puncture into Microtainer tubes (SST®, BD Biosciences, Bedford, Mass.) and centrifuged at 6000 g for 5 min for serum preparation. For measurement of Evans blue dye levels, mice were perfused through the right ventricle with a phosphate buffer solution, lungs were harvested and weighed, and the Evans blue was extracted by incubation with 100% formamide (Sigma, St. Louis, Mo.) at 50° C. for 18-24 hours. The levels of Evans blue in the serum and the tissue supernatant were then determined by measuring the absorbance at 620 nm. The reading at 620 nm ($E_{620}$) was corrected for the presence of contaminating heme pigments in the samples by measuring the absorbance at 740 nm ($E_{740}$) and using the correction formula $E_{620}=E_{620}-(1.426 \times E_{740}+0.030)$. The amount of Evans blue in the samples was then calculated using a standard curve obtained with known amounts of Evans blue. The results were normalized by considering the mean level of Evans blue measured in LPS-treated mice as 100%.

Example 4

In Vitro Screening for Metabolic Stability with Human Liver Microsomes

A standard screening of compounds for in vitro metabolic stability with human liver microsomes was done at 5 µM of compound using commercially available, calibrated human liver microsomes (BD Biosciences, Bedford, Mass.) and an NADPH-regenerating system. [D. Ackley, K. Rockich and T. Baker. in (Caldwell, Z.Y.a.G. W., ed.) Methods in pharmacology and toxicology optimization in drug discovery: in vitro methods, Humana Press Inc., Totowa, N.J. 2004, pp. 151-62.] Briefly, reaction mixtures were prepared in 0.1 M potassium phosphate buffer and contained 1.6 mg/ml microsomal protein, 5 µM test compound, 1.3 mM NADPH, 3.3 mM MgCl$_2$, 0.4 U/ml glucose-6-phosphate dehydrogenase, and 3.3 mM glucose-6-phosphate in a total volume of 300 µl. Reactions were incubated for 10 and 30 minutes at 37° C. and halted by addition of cold acetonitrile. The mixture was centrifuged at 10000 g for 10 min and 20 µl of supernatant was analyzed by HPLC to quantify the percentage of the initial amount of compound remaining after incubation. The HPLC mobile phase consisted of 5% acetonitrile in water as reagent A and 80% acetonitrile/0.08% formic acid/water as reagent B at a flow rate of 0.2 ml/min. The gradient consisted of the following variations in % B: begin with % B at 0 for 2 min, 0-100% from 2 to 22 min, isocratic until 24 min. Peak quantification was done based upon absorption measurements at 260 nm relative to a standard curve obtained by serial dilutions of known amounts of compounds.

Example 5

Small-Molecule Inhibitor Design and Synthetic Strategy

The use of a dual headed scaffold with a 6-phenyl-3-amino-pyridazine group at one end and a variable amine at the other end was selected as a starting point for compound development. [M. S. Wainwright, J. Rossi, J. Schavocky, S. Crawford, D. Steinhorn, A. V. Velentza, M. Zasadzki, V. Shirinsky, Y. Jia, J. Haiech, L. J. Van Eldik and D. M. Watterson, Proc. Natl. Acad. Sci. USA 100 (2003) 6233-8; A. V. Velentza, M. S. Wainwright, M. Zasadzki, S. Mirzoeva, A. M. Schumacher, J. Haiech, P. J. Focia, M. Egli and D. M. Watterson, Bioorg. Med. Chem. Lett. 13 (2003) 3465-70.] Compound 1 is the selective MLCK inhibitor used to validate the results with the MLCK210 KO mice. Compound 2 is a less selective MLCK inhibitor with an $IC_{50}$ value of 2.7 μM that also inhibits the structurally-related, calmodulin regulated DAPK and the physiological pathway relevant PKC. With respect to certain non-limiting embodiments of this invention, compound selectivity can be considered in the context of a value of 10-fold better $IC_{50}$ for MLCK inhibition, as compared to DAPK, PKC and PKA.

TABLE 1

In vitro inhibition of kinases

| | $R_3$ | $R_6$ | n | X | MLCK (μM) | DAPK (μM) | PKC (μM) | PKA (μM) | log S (mol/L)* |
|---|---|---|---|---|---|---|---|---|---|
| 1 | H | Cl | 10 | 6-methyl-3-phenylpyridazine | 5** | >100 | >100 | >100* | -3.54 |
| 2 | H | Ph | 10 | 6-methyl-3-phenylpyridazine | 2.7 ± 1.6 | 22* | 3** | >100** | -4.09 |
| 5 | H | Ph | 10 | imidazolylethyl | 6.3 ± 3.1 | 271 | 166 | >1000 | -2.09 |
| 6 | H | Ph | 10 | pyrrolidinylethyl | 13.3 ± 8.1 | >1000 | 414 | >1000 | -0.71 |
| 7 | H | Ph | 8 | pyrrolidinylethyl | >100 | >100 | nd | nd | 0.15 |
| 8 | Me | Ph | 10 | pyrrolidinylethyl | >100 | >100 | nd | nd | -1.20 |
| 9 | H | Ph | 10 | pyrrolidinylethyl | 33.3 ± 1.4 | >1000 | 824 | >1000 | -0.46 |
| 10 | H | Ph | 10 | cyclopentylethyl | 2.5 ± 0.2 | 206 | 68 | >1000 | -3.61 |

*ACD/Solubility DB 9.03. log S is intrinsic solubility of the neutral form of the compounds
**Previously reported [18, 29]
Nd = not determined As a starting point in a synthetic design, the 6-phenyl-3-amino pyridazine portion of compound 2 was retained, and the other lobe of the dual headed molecule was varied. Without limitation to any one theory or mode of operation, molecular modeling suggests that the ability to modulate kinase selectivity with variation of the amine might be due to that portion of the molecule binding within the peptide substrate recognition region of the kinase. Consistent with this model, the starting scaffold, the blocked compound 3 and the reactive precursor compound 4 (see FIG. 1), lack an amine and do not have kinase inhibitor activity under the conditions used. In contrast, compounds 5-10 have an amine at this position, and exhibit kinase inhibitory activity of varying affinity and selectivity (Table 1).

With reference to FIG. 1, the amines coupled to the alkylated 6-phenyl pyridazine scaffold, compound 4, optimally fit criteria relating to production of an inhibitor with low cost-of-goods and ease of synthesis—if first found to be active in kinase inhibition screens. Specifically, the criteria for choice of amines for in-parallel syntheses of candidate inhibitors were that the amines should be primary, aliphatic amines to increase the potential for high yielding, facile coupling reactions. A computed solubility (log S) filter was also used to first synthesize compounds with computed aqueous solubility of log S≦−3 based on the need for more soluble compounds for use as injectables, to facilitate clinical administration through injection or in intravenous fluids.

Implementation of these filters initially led to the choice of two amines—histamine and 2-(1-methylpyrrolidin-2-yl)ethanamine—that resulted in the synthesis of kinase inhibitors compounds 5 and 6, respectively. Based on activity results with these two compounds (Table 1), additional analogs (compounds 7-10) were made in order to gain initial insight into how the structure of these inhibitors was related to kinase inhibitory activity.

Example 6

Synthetic Scheme and Compound Characterization

The synthetic scheme for representative compound 6 is given in FIG. 1. Variations of this scheme were used for the synthesis of the various compounds whose kinase inhibitory activities (Table 1) and in vivo functions were characterized. Specific details and experimental narratives for each intermediate compound and final inhibitor compound are summarized elsewhere, herein. All compounds were screened for purity and evidence of correct product formation by HPLC and mass analysis as described in materials and methods. These results are summarized in Table 2.

TABLE 2

Analytical chemistry for compounds 1-10.

| Compound | ESI | HPLC $t_r$/purity |
|---|---|---|
| 1 | 467.2 (MH+) | 10.78/98% |
| 2 | 424.20 (MH+) | 21.95/90% |
| 3 | 384.4 (MH+) | 21.0/97% |
| 4 | 356.3 (MH+) | 19.0/95% |
| 5 | 225.33 (MH+/2), 449.29 (MH+) | 16.5/>95% |
| 6 | 233.80 (MH+/2) | 14.3/98% |
| 7 | 424.34 (MH+) | 15.03/95% |
| 8 | 240.98 (MH+/2) | 14.16/90% |
| 9 | 227.17 (MH+/2) | 14.41/>98% |
| 10 | 451.67 (MH+) | 20.19/95% |

Example 7a

Selected compounds with kinase inhibitory activity (e.g., compounds 5, 6 and 10) were characterized further to validate structure by HRMS and $^1$H-NMR analysis. The characterizations validated the proposed structures of these three novel compounds, as summarized below.

Example 7b

Compound 5, N-(2-(1H-imidazol-4-yl)ethyl)-11-(6-imino-3-phenylpyridazin-1(6H)-yl)undecanamide, gave the following results consistent with its proposed structure: $^1$H NMR (DMSO-$d_6$), δ8.43 (dd, J=9.5 Hz, J=4 Hz, 1H), 8.00 (s, 2H), 7.87 (d, J=3.5 Hz, 1H), 7.75 (dd, J=9.5 Hz, J=3.5 Hz, 1H), 7.59 (s, 3H), 7.56 (d, J=3.5 Hz, 1H), 4.35 (s, 2H), 3.37 (s, 7H), 3.25 (s, 3H), 2.61 (d, J=3.5 Hz, 2H), 2.03 (d, J=4 Hz, 2H), 1.85 (s, 2H), 1.46 (s, 3H), 1.36 (s, 5H), 1.25 (s, 9H); HRMS ($C_{26}H_{36}N_6O$) expected 448.2945, found 448.2937.

Example 7c

Compound 6, 11-(6-imino-3-phenylpyridazin-1(6H)-yl)-N-(2-(1-methylpyrrolidin-2-yl)ethyl)-undecanamide, gave the following results consistent with its proposed structure: $^1$H NMR (DMSO-$d_6$), δ 8.35 (m, 2H), 7.99 (m, 2H), 7.80 (d, J=5 Hz, 1H), 7.71 (d, J=9 Hz, 1H), 7.58 (d, J=4.5 Hz, 2H), 4.31 (t, J=6.5 Hz, 2H), 3.05 (quintet, J=7 Hz, 2H), 2.99 (m, 1H), 2.55 (s, 3H), 2.23 (s, 2H), 2.12 (m, 2H), 2.02 (t, J=7 Hz, 2H), 1.92 (m, 1H), 1.87 (m, 2H), 1.74 (m, 1H), 1.63 (m, 2H), 1.46 (m, 2H), 1.37 (m, 4H), 1.25 (s, 8H); HRMS ($C_{28}H_{43}N_5O$) expected 465.3462, found 465.3454.

Example 7d

Compound 10, N-(2-cyclopentylethyl)-11-(6-imino-3-phenylpyridazin-1(6H)-yl)undecanamide, gave the following results consistent with its proposed structure: $^1$H NMR (CDCl$_3$), δ8.00 (d, J=9.5 Hz, 1H), 7.83 (m, 2H), 7.78 (dd, J=9 Hz, J=2.5 Hz, 1H), 7.51 (bs, 3H), 5.90 (s, 1H), 4.37 (t, J=6.5, 2H), 3.20 (quartet, J=6 Hz, 2H), 2.13 (t, J=7.5, 2H), 1.91 (m, 2H), 1.74 (s, 2H), 1.57 (m, 4H), 1.48 (d, J=6 Hz, 4H), 1.40 (m, 3H), 1.34 (m, 2H), 1.25 (s, 10H), 1.07 (s, 2H); HRMS ($C_{28}H_{42}N_4O$) expected 450.3353, found 450.3346.

Example 8a

Detailed Synthetic Narrative

The starting scaffold (compound 4) that was used to generate inhibitors by reaction with the various coupled amines was synthesized as described previously in the literature. [A. V. Velentza, M. S. Wainwright, M. Zasadzki, S. Mirzoeva, A. M. Schumacher, J. Haiech, P. J. Focia, M. Egli and D. M. Watterson, Bioorg. Med. Chem. Lett. 13 (2003) 3465-70.] Briefly, 11-bromo undecanoic acid (10 g, 37.7 mmol) was placed in 150 mL ethanol with 4N HCl in dioxanes (10 mL, 0.25 mL/mmol acid) and stirred for 48 h at room temperature. The ethanol was removed under reduced pressure leaving the product as a yellow oil. The oil was used without further purification in the next step. Ethyl 11-bromo undecanoate (8 g, 27.3 mmol) was dissolved in 30 mL DMF and heated to 80° C. Subsequently, 0.77 equiv of 3-amino-6-phenyl pyridazine (3.6 g, 21 mmol) was dissolved in minimal DMF and added dropwise to the solution. The reaction was capped and stirred for 8 h. After the reaction was cooled to ambient temperature and diluted with water, the mixture was poured slowly onto ether (100 mL) giving a white solid. The solid was filtered and rinsed with hexanes to afford the product, compound 3, in 86% yield. To deprotect the ethyl ester, compound 3 (6.8 g, 17.8 mmol) was then dissolved in 90 mL glacial acetic acid and 18 mL of 12 N HCl and refluxed for 5 h. The solvent was removed under reduced pressure, and the resulting residue triturated with ether to form a pink solid. The solid was dissolved in ethyl acetate and precipitated out with hexanes to give the product, compound 4, as a white solid in 95.2% yield. The same procedure was followed starting with 8-bromooctanoic acid instead of 11-bromoundecanoic acid for the synthesis of compound 7. The protection of the acid proceeded with 69% yield and was used without further purification in the alkylation step. The alkylation step was performed in 71% yield followed by deprotection of the ethyl ester in 97% yield.

Example 8b

For the synthesis of compound 8,3-chloro-6-phenyl pyridazine (0.5 g, 2.6 mmol) was aminated at the 3-position in a reaction vessel with 5 equiv methylamine HCl (877 mg, 13 mmol) and 5 equiv triethylamine (1.5 mL, 13 mmol). The reactants were dissolved in 15 mL butanol and purged with argon. The vessel was capped and placed at 130° C. for 24 h. Upon cooling to ambient temperature, white crystalline needles formed and were filtered off. Water was then added to the filtrate, forming a white solid precipitate, which was filtered to give the product in 83% yield. This compound was then alkylated with ethyl 11-bromoundecanoate and deprotected as described above with comparable yields.

Example 8c

For the amination reactions, both conventional and microwave coupling reactions were explored. The conventional coupling proceeded in moderate yields, using standard amination coupling conditions. Briefly, compound 4 was placed in a capped vessel and dissolved in dry 1-methyl-2-pyrrolidinone (NMP). 1.1 equiv 1-hydroxy-7-azabenzotriazole (HOAT) and 4 equiv of diisopropyl ethyl amine (DIEA) were added. The vessel was purged with argon, capped, and cooled to 0° C. 1.1 equiv 1-ethyl-3-(3-dimethylamino propyl) carbodiimide hydrochloride (EDC) was then added, and the vessel purged again with argon. The mixture was stirred at 0° C. for 45 minutes, and 1.5 equiv of the amine was added. The reaction mixture was purged with argon, removed from the ice bath and allowed to stir at room temperature until complete. This method was applied for compounds 5 through 8.

Example 8d

For compound 5, the reaction was complete after 48 h, and water (10 mL) was added to the solution, forming a suspension. The suspension was filtered to give a white solid in 47.8% yield. Compound 6 was also complete after 48 h, and the red orange solution was diluted with water (10 mL) to give a cloudy orange suspension. The aqueous phase was washed with ether (2×5 mL) and extracted with chloroform (3×15 mL). The chloroform layers were combined, dried over magnesium sulfate and evaporated under reduced pressure. The residue was then dissolved in ethyl acetate and washed with water (3×30 mL) and sodium bicarbonate (2×30 mL) to remove residual amine. The ethyl acetate was then dried and evaporated under reduces pressure to give a red-orange oil. The oil was purified with solid phase extraction (SPE) using equilibrated $C_{18}$ Sep-Pak® cartridges (Waters, Mass.), and eluted with 25% acetonitrile in 0.1% formic acid to give a pale orange solid in 46% yield.

Example 8e

Compound 7 was also a red-orange mixture, but did not form a suspension upon the addition of water. The aqueous mixture was washed with ethyl acetate (3×20 mL) and chloroform (3×30 mL), and then evaporated under reduced pressure, producing a white solid in 30% yield.

Example 8f

Amination of compound 8 was complete in 24 h, and water was added to the reaction mixture to form a suspension. The mixture was extracted with chloroform (3×25 mL), and the organic layers were combined and subsequently washed with sodium bicarbonate (5×50 mL) to remove unreacted acid starting material. The organic layer was then dried with magnesium sulfate and evaporated under reduced pressure. The solid was purified with SPE and eluted with 25% acetonitrile in 0.1% formic acid to afford product in 41% yield.

Example 8g

Due to the yields seen for conventional coupling, microwave coupling was also investigated. Following the procedure of Santagada et al., compound 4 was placed into a 10 mL microwave reaction vessel with 1.1 equiv 2-(1H-benzotriazole-1-yl)-1,1,3,3,-tetramethyluronium hexafluorophosphate (HBTU), 1.1 equiv HOAT, 2 equiv DIEA and 1 equiv amine. [V. Santagada, F. Fiorino, E. Perissutti, B. Severino, V. De Filippis, B. Vivenzio and G. Caliendo, Tetrahedron Lett 42 (2001) 5171-73.] The reagents were dissolved in 3 mL NMP and purged with argon. The vessel was sealed and placed in the microwave first for 15 minutes at 55° C. (200 W) and then for 20 minutes at 60° C. (300 W).

Example 8h

Compound 6 was synthesized by this method to compare the microwave and conventional syntheses directly. After 35 minutes of reaction time, the mixture was poured over bicarbonate (10 mL) and extracted with ethyl acetate (5×20 mL). The ethyl acetate layers were combined, dried with magnesium sulfate, and evaporated under reduced pressure. The remaining red orange oil was purified with SPE and eluted with 25% acetonitrile in 0.1% formic acid to afford a pale orange solid in 90% yield. Compared to the conventional synthesis, the yield doubled under the microwave synthesis conditions.

Example 8i

Based on the initial microwave results, analogs 9 and 10 were also synthesized via microwave heating. For compound 9, the Boc-protected pyrrolidine was coupled onto the compound 4. When the reaction was complete, the yellow solution was poured onto sodium chloride (20 mL) and extracted with ethyl acetate (3×20 mL). The organics were collected, dried over magnesium sulfate, and evaporated under reduced pressure to afford the product as brown oil in 96.4% yield. The product was confirmed by ESI and used without further purification in the deprotection step. The oil (300 mg, 0.54 mmol) was dissolved in a solution of 3M HCl in ethyl acetate and stirred at room temperature. After 30 minutes no starting material remained, and the reaction mixture was evaporated under reduced pressure to afford the product as yellow oil. The compound was then purified by SPE and eluted with 25% acetonitrile in 0.1% formic acid in 86% yield.

Example 8j

The synthesis of compound 10 followed the same overall microwave procedure. At the end of the reaction, the orange mixture was poured over sodium chloride (20 mL) and extracted with ethyl acetate (3×20 mL). The organic layers were then combined and washed with water (5×30 mL) and sodium bicarbonate (3×30 mL). The organic layers were combined and dried with magnesium sulfate and evaporated under reduced pressure to provide the compound as a pale brown solid. The compound was then purified with SPE and eluted with 50% acetonitrile in 0.1% formic acid in 79% yield.

Example 9a

Screening for In Vitro Inhibitory Activity

Final compounds were initially screened for concentration dependent inhibition of MLCK (Table 1). Compound 5 inhibits MLCK with an $IC_{50}$ value of 6.3 µM and is more selective than compounds 1 or 2. Compound 6 inhibits MLCK with a comparable $IC_{50}$ of 13.3 µM and is also highly selective for MLCK. In the case of protein kinase inhibitors, values for $IC_{50}$ that approximate or are better than the value for the ATP or peptide substrate Km values suggest such selective compounds to be candidates for further in vivo testing of function.

Example 9b

Aliphatic amines such as that incorporated into compound 6 had not been previously examined, suggesting features of compound 6 might provide some insight into a structural relationship with MLCK activity. In an attempt to enhance solubility and decrease the number of rotatable bonds in the molecule, compound 7 was synthesized with an alkyl chain that is 8 carbons long, versus the 11 carbons in compound 6 (Table 1). However, it was observed that shortening the carbon chain diminished the inhibitor activity of the compound for MLCK. This was also observed for an 8 carbon analog of compound 5 (data not shown). The next variation was designed to simplify the electronics of the pyridazine core, and potentially confer greater stability of the compound. This was done by methylating the free amino group on the pyridazine ring in compound 8. However, when tested in vitro, the inhibitory activity of compound 8 against MLCK decreased (Table 1).

Example 9c

The observation that changing the amine moiety on the pyridazine ring from a primary to secondary amine drastically reduced the activity of the inhibitor for MLCK prompted investigation into the tertiary nitrogen present in a 2-(1-methylpyrrolidin-2-yl) moiety. To investigate this, compound 9 was designed without the methyl group. A small drop in activity was observed, implying that the amide substituent has less effect on compound activity than the exocyclic amine of the pyridazine ring. To further explore the role of the nitrogen in the pyrrolidine group, compound 10 was designed with no nitrogen present, e.g., a carbocycle group. Compound 10 was found to be selective for MLCK and more active in vitro than the parent compound 6 in MLCK inhibition (2.5 µM) (Table 1). Of the compounds tested, compound 6 appears, therefore, to be the best overall inhibitor in terms of in vitro activity, selectivity and molecular properties and was given priority for in vivo screening of function.

Example 10

In Vivo Screening for Function

Figure 2:
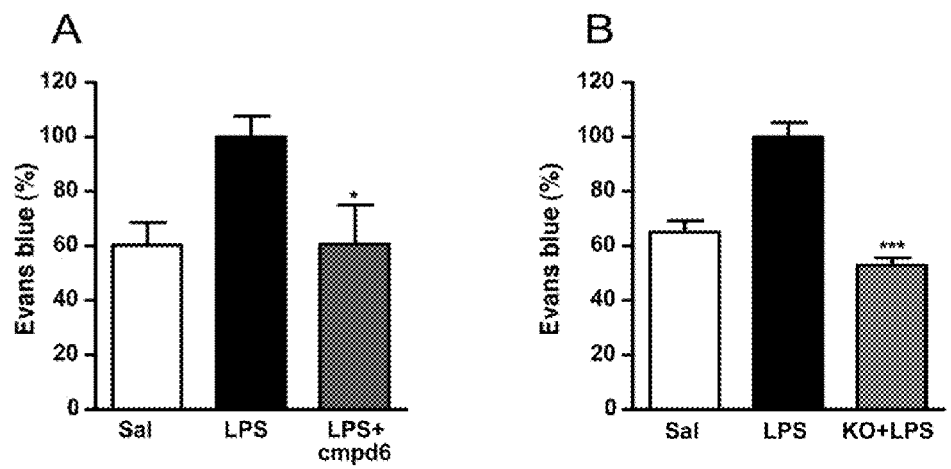

With the hypothesis that an MLCK inhibitor can inhibit pulmonary vascular leak resulting from increased endothelial permeability, compound 6 was tested in vivo compound 6 for protection from LPS induced vascular leak in the lungs. Pulmonary vascular leak was assessed by measuring the extravasation of Evans blue dye into the lung tissue after an injurious exposure to LPS. The injection of LPS in the mice induced a significant increase in the Evans blue level in the lung tissue, indicating an increase in vascular leak in this tissue (FIG. 2). The results screen showed that compound 6 was efficacious in vivo to reduce LPS-induced pulmonary vascular leak, comparable to the level measured in the lungs of saline-treated control mice (FIG. 2A). This level of suppression is comparable to that seen with MLCK 210 KO mice. This control experiment is shown in FIG. 2B.

Example 11

Human Liver Microsome Stability

To extend the structural utility of such compounds in human studies and justify further refinement, compound 6 was subjected to a standard HLM metabolic stability screening assay. [D. Ackley, K. Rockich and T. Baker in (Caldwell, Z.Y.a.G. W., ed.) Methods in pharmacology and toxicology optimization in drug discovery: in vitro methods, Humana Press Inc., Totowa, N.J. 2004, pp. 151-62.] FIG. 3 shows that compound 6 is very stable in the HLM assay, as the levels of compound measured in the HLM mixture did not decrease up to 30 minutes of incubation. As a comparative control, compound 10 was tested for stability in the HLM assay. As shown, the amount remaining at 10 and 30 minutes is significantly lower than compound 6. Efficacy and metabolic stability are independent but related events and one cannot extend HLM metabolic stability results to the prediction of in vivo stability in humans, but the results further indicate the development promise of compound 6.

Example 12

Synthesis of Pyridazine Intermediates

Representative aminopyridazine intermediates useful in preparation of the compounds of this invention are synthesized from chloride precursors via the corresponding pyridazinones (Scheme 1). The amino pyridazines are synthesized following previously reported methods (Wermuth C G et al., 1987) with a hydrazine intermediate (Scheme 1). Alternatively, the 6-phenyl 3-amino pyridazine can be synthesized via a Suzuki reaction (Maes, B U W et al., 2000) of 3-chloro 6-amino pyridazine with phenyl boronic acid (Scheme 2).

Scheme 1:

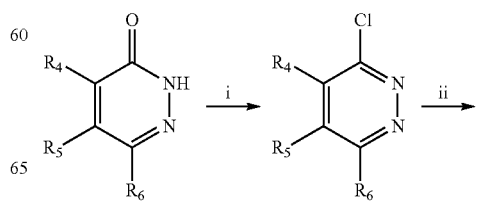

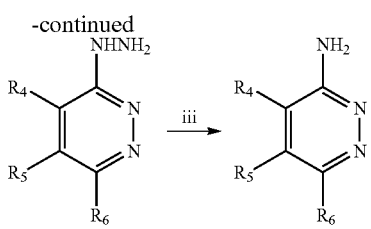

i) POCl₃, reflux
ii) NH₂NH₂, BuOH, reflux,
iii) H₂-Raney Ni—MeOH

Scheme 2:

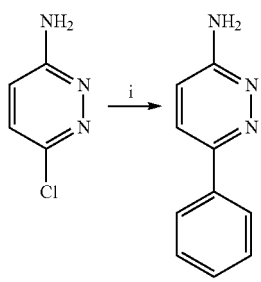

i) Pd(Ph₃P)₄, Toluene, Bicarbonate, phenyl boronic acid, 120° C., 24 h

The intermediates of the sort that can be made via scheme 1 are shown below, any of which as can be used interchangeably in the following synthetic schemes or elsewhere as described, herein.

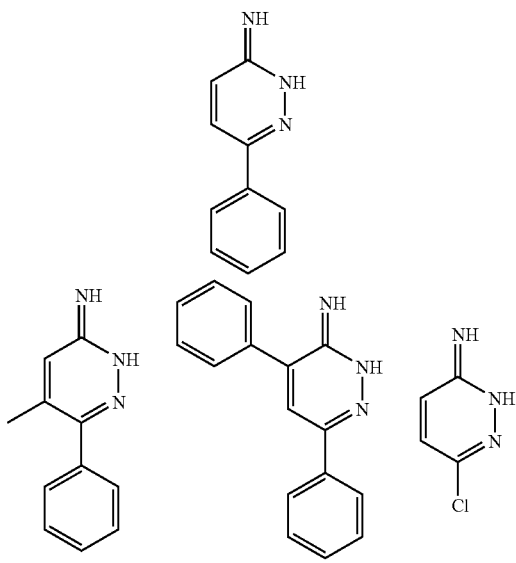

Example 13

FIG. 1 shows synthesis of one linker moiety useful in conjunction with compounds of this invention. Illustrating another representative linker moiety, refer to Scheme 3. A bromo alcohol is protected following literature procedure (Grube, 2006). Briefly, the alcohol is placed in methylene chloride, and 1.5 equivalents of DHP and 0.01 equiv pyridinium p-toluene sulfonate (PPTS) are added and stirred at ambient temperature for 16 h. Upon completion, the solution is washed with bicarbonate, and the organic layer is dried with magnesium sulfate and evaporated under reduced pressure to give the product as an oil that is stored out of the light. The oil is then dissolved in DMF and the pyridazine is added in DMF dropwise to the solution. The reaction is capped, heated to 80° C. and allowed to stir for 6-8 hours. When the reaction is complete, the mixture is cooled and poured over ether to afford a brown solid that is stored away from the light. The deprotection is then performed following literature procedure (Guan, 2002). Briefly, the solid is dissolved in methanol: tetrohydrofuran (1:1 v/v) followed by addition of 1 equiv of PTTS. The mixture is heated for 4 h at 60° C. or until complete. Upon completion, the reaction is cooled, and the solvents dissolved under reduced pressure. The residue is taken up in basic water (pH=8) and extracted with ethyl acetate to give a white solid. The resulting intermediate can then be reacted, as shown in the following examples.

Scheme 3.

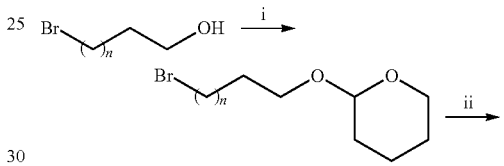

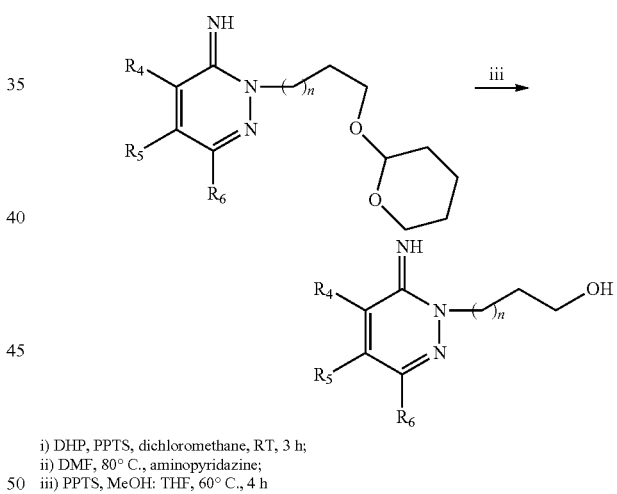

i) DHP, PPTS, dichloromethane, RT, 3 h;
ii) DMF, 80° C., aminopyridazine;
iii) PPTS, MeOH: THF, 60° C., 4 h Example 14

The intermediate of example 13 can be converted to the corresponding primary amine following standard Mitsunobu conditions (Mitsunobu, O et al., 1972). See, Scheme 4. Briefly, the alcohol is placed in THF with 1 equiv each of pthalamide, diethyl azodicarboxylate (DEAD) and triphenyl phosphine. The reaction is allowed to stir at ambient temperature and monitored for transformation to product. The solvent is evaporated under reduced pressure and the residue purified over column chromatography. The pthalamide is then cleaved with an excess of hydrazine in ethanol at 60° C. for 12 h to form the amine.

Scheme 4:

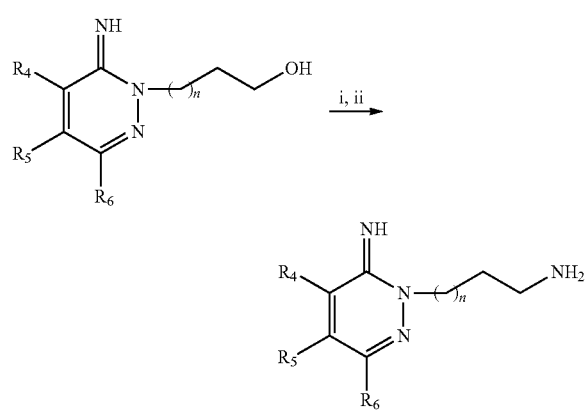

i) DEAD, Ph₃P, phthalamide;
ii) hydrazine

Example 15

The amine of example 14 can couple to a range of available acids (e.g., without limitation Chart 1) via conventional amide bond formation methods. A representative inhibitor is shown below.

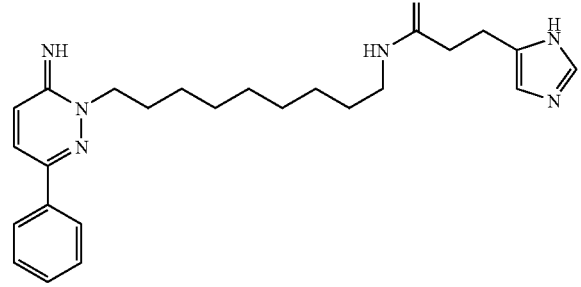

Chart 1: Representative Acids for Amination Reactions.

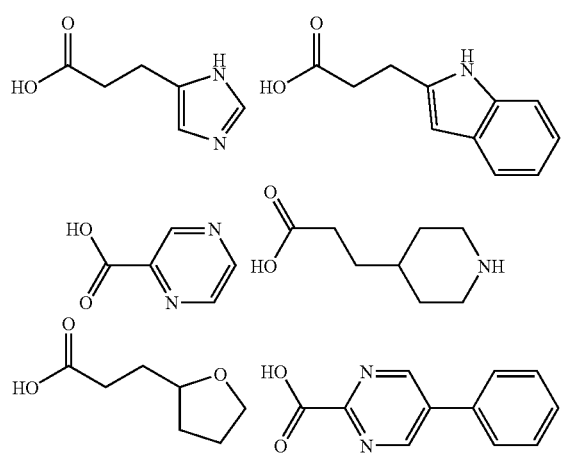

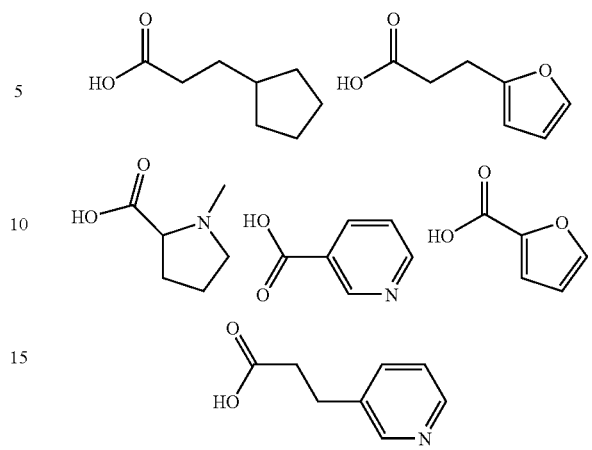

Example 16

The intermediate in example 13 can also be converted to tertiary amine via a mesylate, as show in Schemes 5 and 6.

Scheme 5

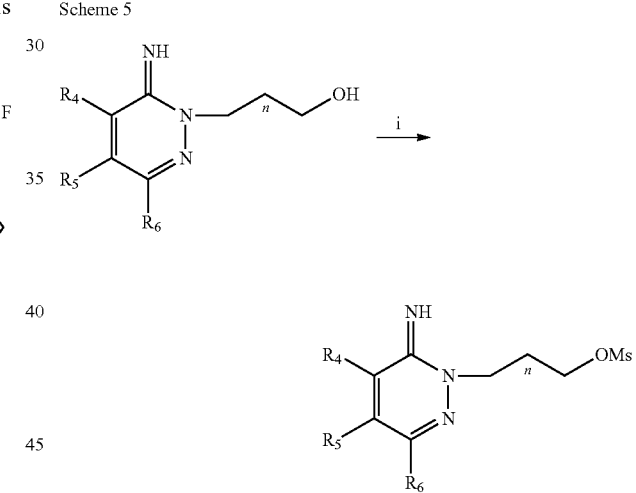

i) methanesulfonyl chloride, pyridine, 2 h

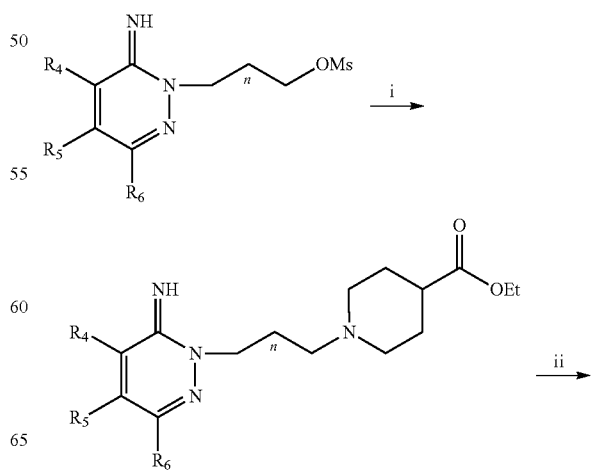

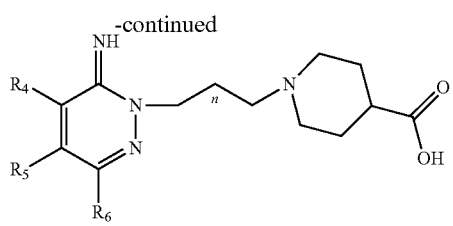

i) Piperidine-4-carboxylic acid ethyl ester, THF, 80° C.;
ii) HCl, AcOH, reflux, 6 h The intermediate is formed from the alcohol via a mesylate (Li, H et al., 2006). The alcohol is placed in dry pyridine, and 3 equiv methane sulfonyl chloride is added dropwise. The reaction is stirred at ambient temperature for 2 h or until completion of the reactions. Upon completion, the pyridine is removed under reduced pressure and the residue is take up in chloroform and washed with sodium bicarbonate. The chloroform is then dried over sodium sulfate and evaporated under reduced pressure. Purification over silica gel is performed if necessary. The mesylate is then aminated by adding the mesylate to a flask containing an excess (10 equiv) of amine in THF. The mixture is heated at 80° C. for 30 min to 1 h, or until the reaction is complete. The reaction is then cooled to ambient temperature, and solvent evaporated under reduced pressure. The residue is then purified with silica gel chromatography to give product. The ester of the piperadine carboxylate is deprotected in >90% yield by refluxing in HCl and acetic acid for 6-24 h.

Scheme 6.

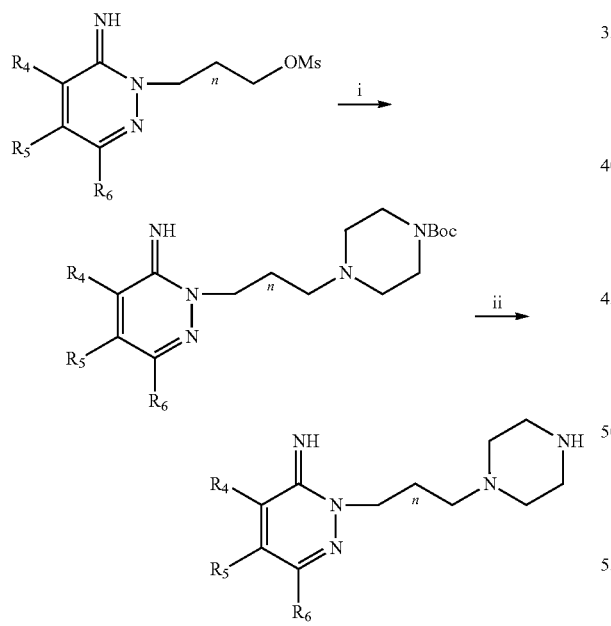

i) tert-butyl piperazine-1-carboxylate, THF, 80° C.;
ii) HCl, EtOAc, 4 h

Example 17

The mesylate can also be formed as in example 16 and then aminated as in example 16 with 1-boc-piperazine. The boc-piperazine is subsequently deprotected with 3M HCl in ethyl acetate at ambient temperature for 1 h. When complete, the solvents are evaporated under reduced pressure, and the residue is triturated with ether (Scheme 6).

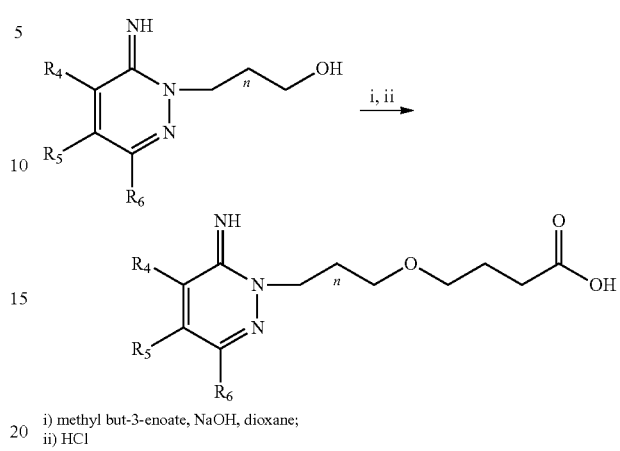

i) methyl but-3-enoate, NaOH, dioxane;
ii) HCl

Example 18

The alcohol in example 13 can also be reacted to provide a linker with an oxygen (Hickmann E, 1991). The alcohol and methyl but-3-enoate is placed in benzyltrimethylammonium hydroxide and stirred at ambient temperature until the reaction is complete. The reaction is quenched with ice water and extracted with methylene chloride to give the methyl ester. The ester is then refluxed in HCl and acetic acid for 6 h as in example 16. The solvent is then evaporated under reduced pressure, and the residue triturated with ether to give the product.

Example 19

The intermediate from example 16 can be coupled to a variety of amines (e.g. without restriction, Chart 2) with methods demonstrated in examples 8. Chart 2.

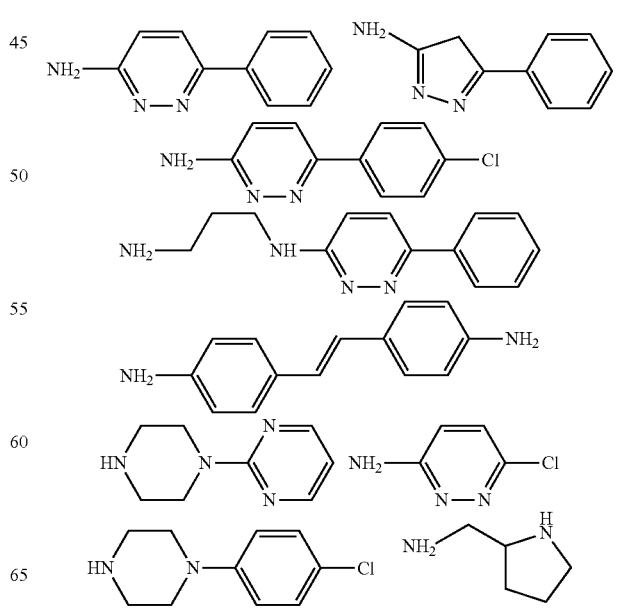

-continued

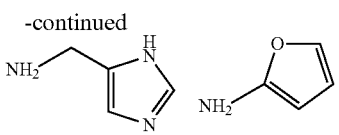

Example 20

The intermediate from example 18 can be coupled to a range of acids (e.g. without limitation, Chart 1) as is seen in example 15.

Example 21

The intermediate from example 18 can be coupled to amines such as those in chart 2, following methods as shown in examples 8.

As demonstrated above, this invention provides a class of small-molecule MLCK inhibitors with more attractive cost-of-goods and tunable molecular properties, consistent with effective therapeutic use as described herein. As illustrated above, in accordance with various other aspects and embodiments of this invention, representative compounds have appropriate in vivo function, as illustrated by attenuating endotoxin induced pulmonary vascular leak in mice.

We claim:

1. A method of inhibiting myosin light chain kinase activity, said method comprising:
providing a medium comprising a myosin light chain kinase; and
contacting said medium with a compound of a formula

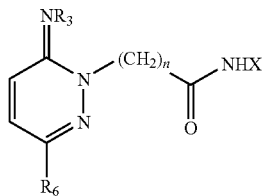

wherein $R_3$ is selected from H and alkyl moieties; $R_6$ is selected from H, halo, alkyl, aryl and heterocyclic moieties; n is an integer from 8 to 14; and X is $(CH_2)_2Y$, where Y is selected from substituted and unsubstituted pyrrolidinyl, substituted and unsubstituted pyrrolyl, substituted and unsubstituted pyrazolyl, substituted and unsubstituted imidazolyl and substituted and unsubstituted cyclopentyl moieties; and salts thereof, said compound in an amount sufficient to at least partially inhibit said kinase activity.

2. The method of claim 1 wherein said contact is in vivo.

3. The method of claim 2 contacting at least one of epithelial and endothelial tissue exhibiting barrier dysfunction.

4. The method of claim 3 wherein the at least one of epithelial and endothelial tissue exhibiting barrier dysfunction that is contacted is injured pulmonary tissue.

5. The method of claim 3 wherein said compound is in a pharmaceutical composition.

6. The method of claim 1 wherein $R_3$ is hydrogen, $R_6$ is halo or phenyl, n is 10, and X is selected from 6-phenylpyridazin-3-yl, 1H-imidazol-2-yl methyl, 1-methylpyrrolidin-2-yl methyl, pyrrolidin-2-yl methyl and cyclopentyl methyl.

7. The method of claim 6 wherein the compound is selected from:
11-(6-imino-3-phenylpyridazin-1(6H)-yl)-N-(6-phenylpyridazin-3-yl)undecanamide;
11-(3-chloro-6-iminopyridazin-1(6H)-yl)-N-(6-phenylpyridazin-3-yl)undecanamide;
N-((1H-imidazol-2-yl)methyl)-11-(6-imino-3-phenylpyridazin-1(6H)-yl)undecanamide;
11-(6-imino-3-phenylpyridazin-1(6H)-yl)-N-((1-methylpyrrolidin-2-yl)methyl)undecanamide;
11-(6-imino-3-phenylpyridazin-1(6H)-yl)-N-(pyrrolidin-2-ylmethyl)undecanamide; and
N-(cyclopentylmethyl)-11-(6-imino-3-phenylpyridazin-1(6H)-yl)undecanamide.

8. A method of treating progression of acute tissue injury, said method comprising:
providing at least one of epithelial and endothelial tissue with barrier dysfunction, and
contacting said tissue with a compound of a formula

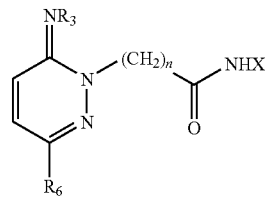

wherein $R_3$ is selected from H and alkyl moieties; $R_6$ is selected from H, halo, alkyl, aryl and heterocyclic moieties; n is an integer from 8 to 14; and X is $(CH_2)_2Y$, where Y is selected from substituted and unsubstituted pyrrolidinyl, substituted and unsubstituted pyrrolyl, substituted and unsubstituted pyrazolyl, substituted and unsubstituted imidazolyl and substituted and unsubstituted cyclopentyl moieties; and salts thereof, said compound in a therapeutically sufficient amount.

9. The method of claim 8 wherein said contact is in vivo.

10. The method of claim 9 wherein the at least one of epithelial and endothelial tissue exhibiting barrier dysfunction that is contacted is injured pulmonary tissue.

11. The method of claim 9 wherein said therapeutic amount is selective for MLCK inhibition over inhibition of at least one of DAPK, PKC and PKA.

12. The method of claim 11 wherein said MLCK inhibition is confirmed against MLCK210 (KO) mice.

13. The method of claim 8 wherein $R_3$ is hydrogen, $R_6$ is halo or phenyl, n is 10, and X is selected from 6-phenylpyridazin-3-yl, 1H-imidazol-2-yl methyl, 1-methylpyrrolidin-2-yl methyl, pyrrolidin-2-yl methyl and cyclopentyl methyl.

14. The method of claim 13 wherein the compound is selected from:
11-(6-imino-3-phenylpyridazin-1(6H)-yl)-N-(6-phenylpyridazin-3-yl)undecanamide;
11-(3-chloro-6-iminopyridazin-1(6H)-yl)-N-(6-phenylpyridazin-3-yl)undecanamide;
N-((1H-imidazol-2-yl)methyl)-11-(6-imino-3-phenylpyridazin-1(6H)-yl)undecanamide;
11-(6-imino-3-phenylpyridazin-1(6H)-yl)-N-((1-methylpyrrolidin-2-yl)methyl)undecanamide;
11-(6-imino-3-phenylpyridazin-1(6H)-yl)-N-(pyrrolidin-2-ylmethyl)undecanamide; and
N-(cyclopentylmethyl)-11-(6-imino-3-phenylpyridazin-1(6H)-yl)undecanamide.

15. A method for selective kinase inhibition, said method comprising:

providing a pyridazinylalkaneamide compound of a formula

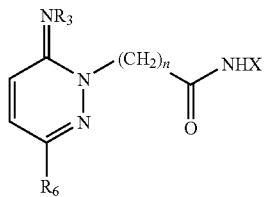

wherein $R_3$ is selected from H and alkyl moieties; $R_6$ is selected from H, halo, alkyl, aryl and heterocyclic moieties; n is an integer from 8 to 14; and X is $(CH_2)_2Y$, where Y is selected from substituted and unsubstituted pyrrolidinyl, substituted and unsubstituted pyrrolyl, substituted and unsubstituted pyrazolyl, substituted and unsubstituted imidazolyl and substituted and unsubstituted cyclopentyl moieties; and contacting said compound with a medium comprising a myosin light chain kinase, said compound in an amount sufficient to at least partially inhibit said kinase activity, said X moiety providing said compound inhibition activity selective over at least one of death-associated protein kinase, protein kinase A and protein kinase C.

16. The method of claim 15 wherein said X moiety provides said compound an aqueous solubility of log S about $\leq -3$.

* * * * *

UNITED STATES PATENT AND TRADEMARK OFFICE
CERTIFICATE OF CORRECTION

PATENT NO. : 8,278,305 B2
APPLICATION NO. : 12/786676
DATED : October 2, 2012
INVENTOR(S) : Daniel Martin Watterson et al.

Page 1 of 1

It is certified that error appears in the above-identified patent and that said Letters Patent is hereby corrected as shown below:

Column 1, Lines 11-13:

"This invention was made with government support under Grant No. NS 047586 awarded by the National Institutes of Health. The government has certain rights in the invention."

should be

--This invention was made with government support under grant number NS047586 awarded by the National Institutes of Health. The government has certain rights in the invention.--

Signed and Sealed this
Eighth Day of January, 2013

David J. Kappos
*Director of the United States Patent and Trademark Office*